(12) United States Patent
Ramanan

(10) Patent No.: US 10,575,758 B2
(45) Date of Patent: Mar. 3, 2020

(54) DIAGNOSIS AND TREATMENT OF RESPIRATORY DISORDERS

(71) Applicant: RedMed Limited, Bella Vista (AU)

(72) Inventor: Dinesh Ramanan, Sydney (AU)

(73) Assignee: ResMed Pty Ltd (AU)

( * ) Notice: Subject to any disclaimer, the term of this patent is extended or adjusted under 35 U.S.C. 154(b) by 520 days.

(21) Appl. No.: 15/117,099

(22) PCT Filed: Feb. 13, 2015

(86) PCT No.: PCT/AU2015/050056
§ 371 (c)(1),
(2) Date: Aug. 5, 2016

(87) PCT Pub. No.: WO2015/120522
PCT Pub. Date: Aug. 20, 2015

(65) Prior Publication Data
US 2017/0164871 A1   Jun. 15, 2017

(30) Foreign Application Priority Data

Feb. 13, 2014   (AU) .................................. 2014900439

(51) Int. Cl.
*A61B 5/08* (2006.01)
*A61B 5/00* (2006.01)

(52) U.S. Cl.
CPC .............. *A61B 5/08* (2013.01); *A61B 5/0816* (2013.01); *A61B 5/4818* (2013.01); *A61M 2230/40* (2013.01); *A61M 2230/42* (2013.01)

(58) Field of Classification Search
None
See application file for complete search history.

(56) References Cited

U.S. PATENT DOCUMENTS

| 4,944,310 A | 7/1990 | Sullivan |
| 6,015,388 A * | 1/2000 | Sackner .................. A61B 5/08 |
| | | 600/529 |

(Continued)

FOREIGN PATENT DOCUMENTS

| CN | 101842128 A | 9/2010 |
| JP | 2003199729 A | 7/2003 |

(Continued)

OTHER PUBLICATIONS

Supplemental European Search Report for Application No. EP15749402, dated Aug. 4, 2017.

(Continued)

*Primary Examiner* — Etsub D Berhanu
*Assistant Examiner* — Jairo H Portillo
(74) *Attorney, Agent, or Firm* — Botos Churchill IP Law LLP

(57) ABSTRACT

A method of a device detects a respiratory effort-related arousal in a respiratory airflow signal of a patient. The method may include computing a measure of consistency of inspiratory flow limitation over a plurality of recent breaths from the signal. The method may further include computing a measure of step change in ventilation indicating a sudden big breath. The method may further include computing a measure indicating a degree of confidence of occurrence of a respiratory effort-related arousal from the measure of consistency of inspiratory flow limitation and the measure of the step change in ventilation.

11 Claims, 21 Drawing Sheets

(56) References Cited

U.S. PATENT DOCUMENTS

| | | | |
|---|---|---|---|
| 6,532,959 B1 | 3/2003 | Berthon-Jones | |
| 2004/0230105 A1* | 11/2004 | Geva | A61B 5/04012 600/301 |
| 2006/0249149 A1* | 11/2006 | Meier | A61B 5/087 128/204.18 |
| 2009/0326349 A1* | 12/2009 | McGonigle | A61B 5/14551 600/323 |
| 2011/0028857 A1* | 2/2011 | Rodriguez Ibanez | A61B 5/08 600/529 |
| 2011/0203588 A1* | 8/2011 | Armitstead | A61M 16/0051 128/204.21 |
| 2012/0179061 A1* | 7/2012 | Ramanan | A61M 16/024 600/538 |

FOREIGN PATENT DOCUMENTS

| | | |
|---|---|---|
| WO | 2004032719 A2 | 4/2004 |
| WO | 2005018737 A1 | 3/2005 |
| WO | 2005051470 A1 | 6/2005 |
| WO | 2006037184 A1 | 4/2006 |
| WO | 2007101297 A1 | 9/2007 |
| WO | 2007147069 A2 | 12/2007 |
| WO | 2008138040 A1 | 11/2008 |
| WO | 2011006199 A1 | 1/2011 |
| WO | 2013152403 A1 | 10/2013 |

OTHER PUBLICATIONS

Rees, K. et al., "Detection of apnoeas, hypopnoeas and arousals by the AutoSet in the sleep apnoea/hypopnoea syndrome", European Respiratory Journal, 1998, vol. 12, pp. 764-769.

International Search Report and Written Opinion for Application No. PCT/AU2015/050056 dated May 25, 2015.

Chinese Office Action issued in corresponding CN application No. 201580018838.6 dated Jan. 8, 2019.

Japanese Office Action issued in corresponding JP application No. 2018-551855 dated Jan. 22, 2019.

* cited by examiner

DIAGNOSIS AND TREATMENT OF RESPIRATORY DISORDERS

1 CROSS-REFERENCE TO RELATED APPLICATIONS

The present application is a national phase entry under 35 U.S.C. § 371 of International Application No. PCT/AU2015/050056 filed Feb. 13, 2015, published in English, which claims priority form Australian Provisional Patent Application No. 2014900439, filed Feb. 13, 2014, all of which are incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE INVENTION

5.1 Field of the Invention

The present technology relates to one or more of the detection, diagnosis, treatment, prevention and amelioration of respiratory-related disorders. In particular, the present technology relates to medical devices or apparatus, and their use for the above purposes.

5.2 Description of the Related Art

5.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

5.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body by doing some or all of the work of breathing. The ventilator support is provided via a patient interface. NIV has been used to treat CSR, OHS, COPD, MD and Chest Wall disorders.

Invasive ventilation (IV) provides ventilatory support to patients that are no longer able to effectively breathe themselves and is provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

5.2.3 Systems

One known device used for treating sleep disordered breathing is the S9 Sleep Therapy System, manufactured by ResMed. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

A system may comprise a PAP Device/ventilator, an air circuit, a humidifier, a patient interface, and data management.

5.2.4 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

5.2.5 Respiratory Apparatus (PAP Device/Ventilator)

Examples of respiratory apparatuses include ResMed's S9 AutoSet™ PAP device and ResMed's Stellar™ 150 ventilator. PAP devices or ventilators typically comprise a flow generator, such as a motor-driven blower or a compressed gas reservoir, and are configured to supply a flow of air or other breathable gases to the airway of a patient. In some cases, the flow of air or other breathable gases may be supplied to the airway of the patient at positive pressure. The outlet of the PAP device or the ventilator is connected via an air circuit to a patient interface such as those described above.

Ventilators or PAP devices typically include a flow generator, an inlet filter, a patient interface, an air circuit connecting the flow generator to the patient interface, various sensors and a microprocessor-based controller. The patient interface may include a mask or a tracheostomy tube as described above. The flow generator may include a servo-controlled motor, volute and an impeller that forms a blower. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the flow generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The apparatus may optionally include a humidifier and/or heater elements in the path of the air delivery circuit. The controller may include data storage capacity with or without integrated data retrieval and display functions.

5.2.6 Monitoring Systems

Polysomnography (PSG) is a conventional system for diagnosis and prognosis of cardio-pulmonary disorders. PSG typically involves the placement of 15 to 20 contact sensors on a person in order to record various bodily signals such as electroencephalography (EEG), electrocardiography (ECG), electrooculograpy (EOG), etc. However, while they may be suitable for their usual application in a clinical setting, such systems are complicated and potentially expensive, and/or may be uncomfortable or impractical for a patient at home trying to sleep.

5.2.7 Respiratory Effort-Related Arousals (RERAs)

In 1999 the AASM Task Force defined RERAs as

A sequence of breaths characterized by increasing respiratory effort leading to an arousal from sleep, but which does not meet criteria for an apnea or hypopnea. These events must fulfil both of the following criteria:
1. Pattern of progressively more negative esophageal pressure, terminated by a sudden change in pressure to a less negative level and an arousal;
2. The event lasts 10 seconds or longer.

In 2000, the study "Non-Invasive Detection of Respiratory Effort-Related Arousals (RERAs) by a Nasal Cannula/Pressure Transducer System" done at NYU School of Medicine and published in Sleep, vol. 23, No. 6, pp. 763-771, demonstrated that a Nasal Cannula/Pressure Transducer System was adequate and reliable in the detection of RERAs.

A RERA detector may be based on a real flow signal derived from a PAP device. For example, a flow limitation measure may be determined based on a flow signal. A measure of arousal may then be derived as a function of the flow limitation measure and a measure of sudden increase in ventilation. One such method is described in PCT Patent Publication no. WO 2008/138040, assigned to ResMed Ltd., the disclosure of which is hereby incorporated herein by reference.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to devices used in the diagnosis, amelioration, treatment or prevention of a respiratory disorder.

Another aspect of the present technology relates to methods used in the diagnosis, amelioration, treatment or prevention of a respiratory disorder.

One form of the present technology comprises methods that detect respiratory effort-related arousals based on a combination of consistent inspiratory flow limitation and "big breath" detection.

Some versions of the present technology may involve a method, such as in one or more processors, for detecting a respiratory effort-related arousal in a respiratory airflow signal of a patient. The method may include receiving in a processor a computed measure of consistency of inspiratory flow limitation over a plurality of recent breaths from the signal. The method may include receiving in a processor a computed measure of step change in ventilation indicating a sudden big breath. The method may include computing in a processor a measure indicating a degree of confidence of occurrence of a respiratory effort-related arousal from the measure of consistency of inspiratory flow limitation and the measure of the step change in ventilation.

In some versions, the method may include, in a processor, calculating the measure of consistency of inspiratory flow limitation over a plurality of recent breaths from the signal. The method may also include, in a processor, calculating the measure of step change in ventilation indicating a sudden big breath. The method may also include computing a maximum measure of inspiratory flow limitation over said plurality of recent breaths, wherein the measure indicating a degree of confidence may be a function of the maximum measure of inspiratory flow limitation. In some cases, the computing the measure indicating the degree of confidence may involve computing a distance between a three-dimensional point whose components are the measure of consistency of inspiratory flow limitation, the measure of a step change in ventilation, and the maximum measure of inspiratory flow limitation and a corner point of a three-dimensional cube. Optionally, the measure of consistency of inspiratory flow limitation may be computed as a fraction of recent flow limitation measures that exceed a predetermined threshold. In some cases, the measure of step change in ventilation may be computed as a difference between a current value of a ventilation ratio and a previous value of the ventilation ratio. The measure of step change in ventilation may be the difference mapped to a range [0, 1]. In some cases, the ventilation ratio may be computed as a mean inspiratory flow rate divided by a measure of current ventilation. The mean inspiratory flow rate may be computed as an average of inspiratory and expiratory tidal volumes divided by an inspiratory time for a current breath.

Optionally, the method may also include comparing the degree of confidence of occurrence of a respiratory effort-related arousal with a predetermined threshold to provide an indication of whether the patient is currently experiencing a respiratory effort-related arousal. The method may also include calculating a respiratory disturbance index from a number of indications of respiratory effort-related arousals in a predetermined interval. The method may also include determining a change to a parameter of a respiratory therapy for the patient based on the measure indicating the degree of confidence.

Some versions of the present technology may include a computer-readable memory storage medium having program instructions encoded thereon configured to cause a processor to perform a method of detecting a respiratory effort-related arousal in a respiratory airflow signal of a patient. The method may include computing a measure of consistency of inspiratory flow limitation over a plurality of recent breaths from the signal. The method may include computing a measure of step change in ventilation indicating a sudden big breath. The method may include computing a measure indicating a degree of confidence of occurrence of a respiratory effort-related arousal from the measure of consistency of inspiratory flow limitation and the measure of the step change in ventilation.

Some versions of the present technology may include a device for detecting a respiratory effort-related arousal in a respiratory airflow signal of a patient. The device may include a sensor configured to provide a signal representative of patient respiratory airflow. The method may include a processor configured to detect a respiratory effort-related arousal. The processor may be configured to compute a measure of consistency of inspiratory flow limitation over a plurality of recent breaths from the signal. The processor may be configured to compute a measure of step change in ventilation indicating a sudden big breath. The processor may be configured to compute a measure indicating a degree of confidence of occurrence of a respiratory effort-related arousal from the measure of consistency of inspiratory flow limitation and the measure of the step change in ventilation.

According to one aspect of the present technology, there is provided a method of detecting respiratory effort-related arousals in a respiratory airflow signal of a patient, comprising the steps of: computing a measure of consistency of inspiratory flow limitation over a plurality of recent breaths from the signal; computing a measure of step change in ventilation indicating a sudden big breath; and computing a measure indicating a degree of confidence of occurrence of a respiratory effort-related arousal from the measure of consistency of inspiratory flow limitation and the measure of the step change in ventilation.

According to another aspect of the present technology, a device for detecting respiratory effort-related arousals in a respiratory airflow signal of a patient comprises a sensor configured to provide a signal representative of patient respiratory airflow, and a processor configured to detect a respiratory effort-related arousal. The processor is configured to: compute a measure of consistency of inspiratory flow limitation over a plurality of recent breaths from the signal; compute a measure of step change in ventilation indicating a sudden big breath; and compute a measure indicating a degree of confidence of the occurrence of a respiratory effort-related arousal from the measure of consistency of inspiratory flow limitation and the measure of the step change in ventilation.

According to a further aspect of the present technology, a computer-readable storage medium has encoded thereon code so as to configure a processor to carry out a method of detecting respiratory effort-related arousals in a respiratory airflow signal of a patient, the method including: computing a measure of consistency of inspiratory flow limitation over a plurality of recent breaths from the signal; computing a measure of step change in ventilation indicating a sudden big breath; and computing a measure indicating a degree of confidence of occurrence of a respiratory effort-related arousal from the measure of consistency of inspiratory flow limitation and the measure of the step change in ventilation.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

FIG. 1A shows a system in accordance with the present technology. A patient 1000 wearing a patient interface 3000, receives a supply of air at positive pressure from a PAP device 4000. Air from the PAP device is humidified in a humidifier 5000, and passes along an air circuit 4170 to the patient 1000. A bed partner 1100 is also shown.

Figure 6A:
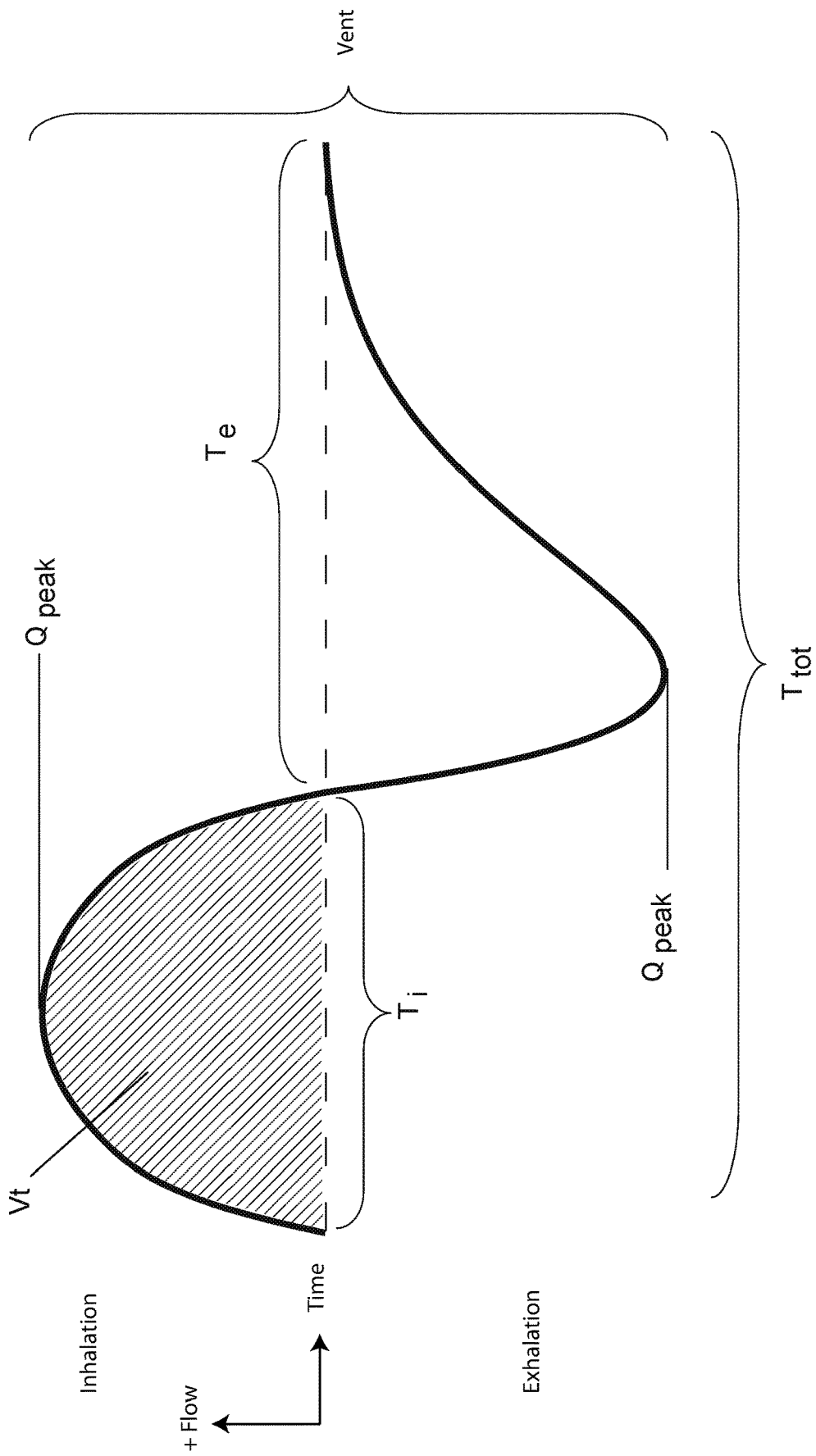

FIG. 6A shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

Figure 6B:
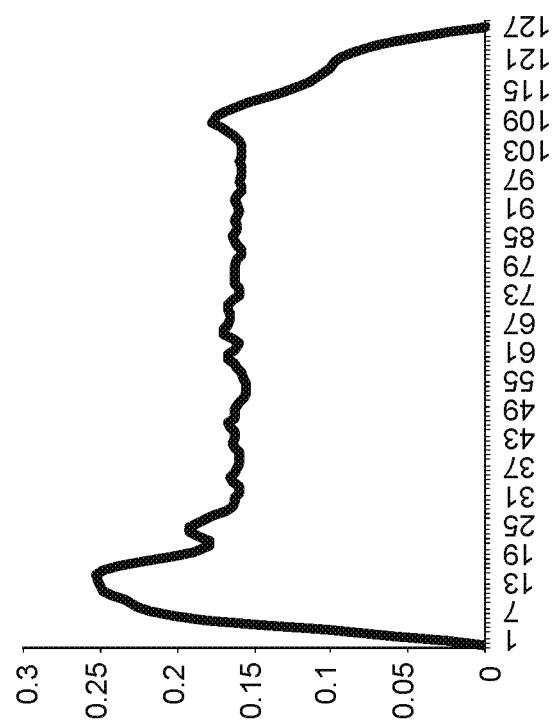

FIG. 6B shows a scaled inspiratory portion of a breath where the patient is experiencing an example of flattened inspiratory flow limitation.

Figure 6C:
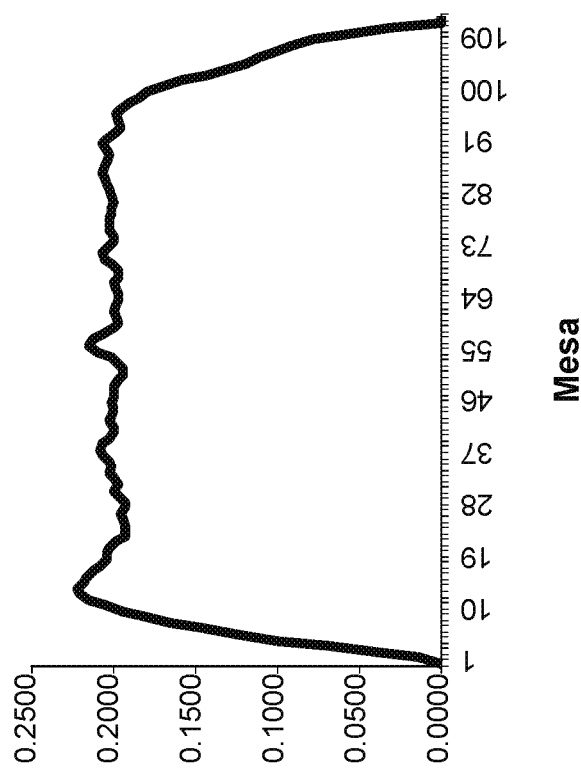

FIG. 6C shows a scaled inspiratory portion of a breath where the patient is experiencing an example of "mesa" flattened inspiratory flow limitation.

Figure 6D:
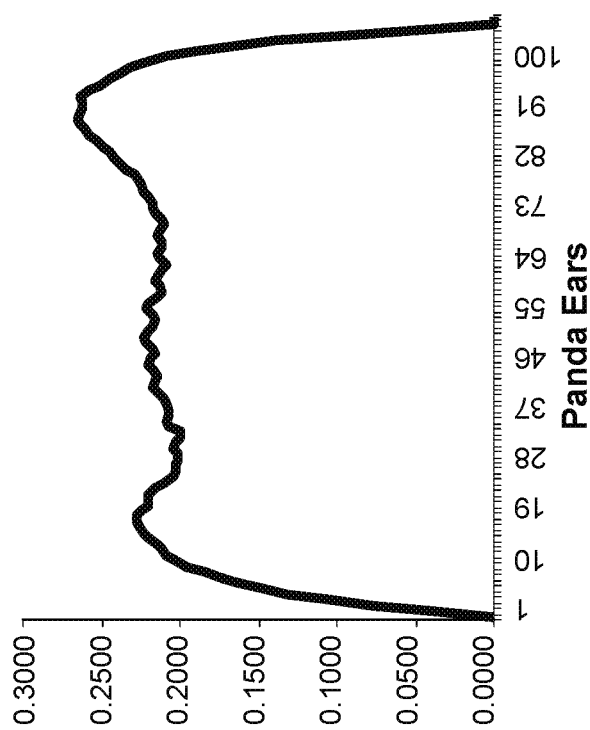

FIG. 6D shows a scaled inspiratory portion of a breath where the patient is experiencing an example of "panda ears" inspiratory flow limitation.

Figure 6E:
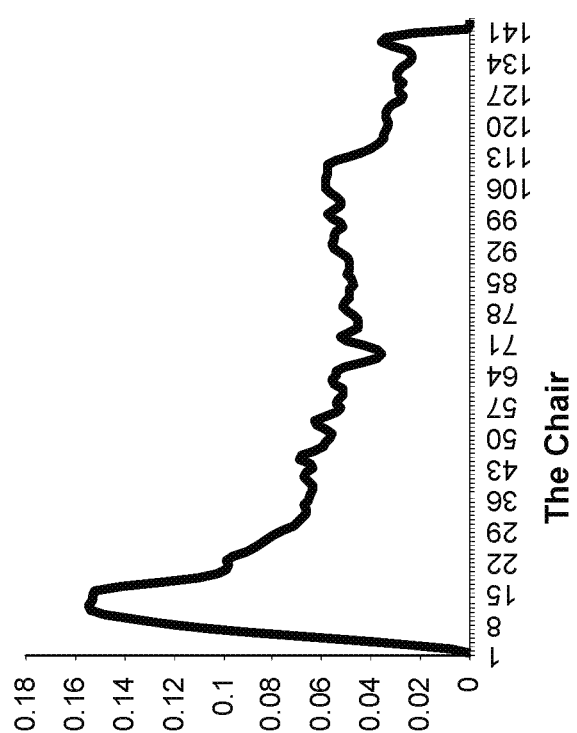

FIG. 6E shows a scaled inspiratory portion of a breath where the patient is experiencing an example of "chair" inspiratory flow limitation.

Figure 6F:
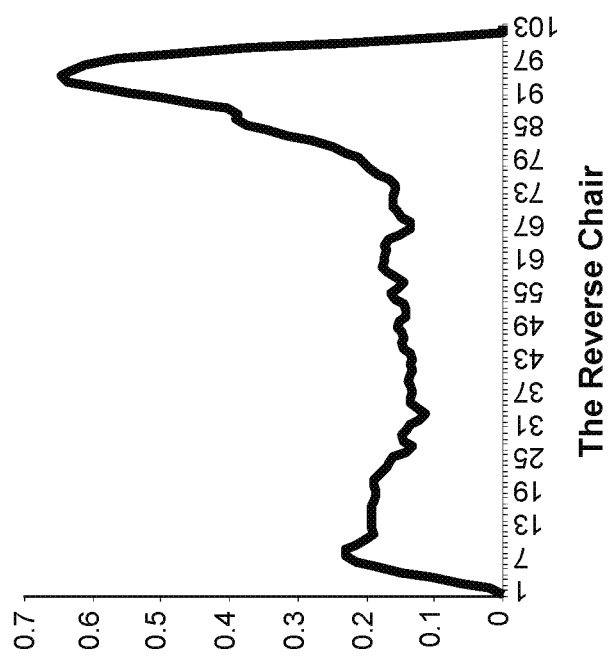

FIG. 6F shows a scaled inspiratory portion of a breath where the patient is experiencing an example of "reverse chair" inspiratory flow limitation.

Figure 6G:
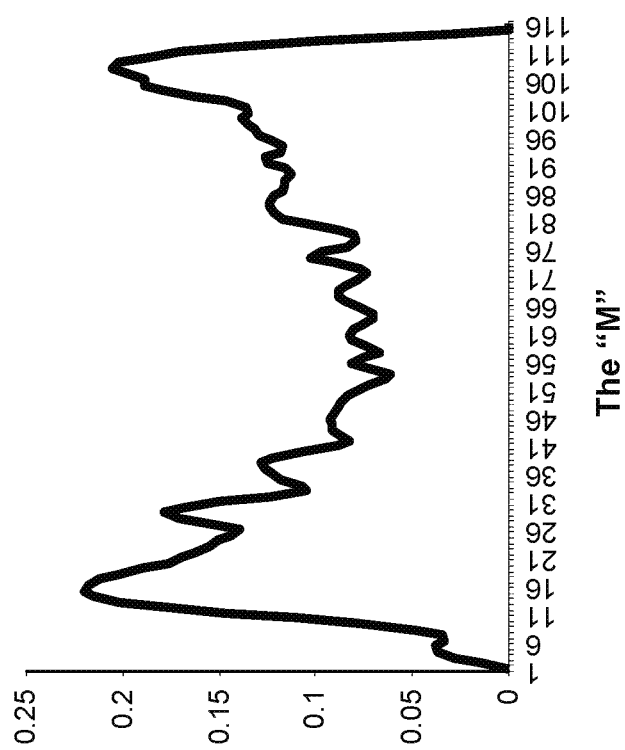

FIG. 6G shows a scaled inspiratory portion of a breath where the patient is experiencing an example of "M-shaped" inspiratory flow limitation.

Figure 1A:
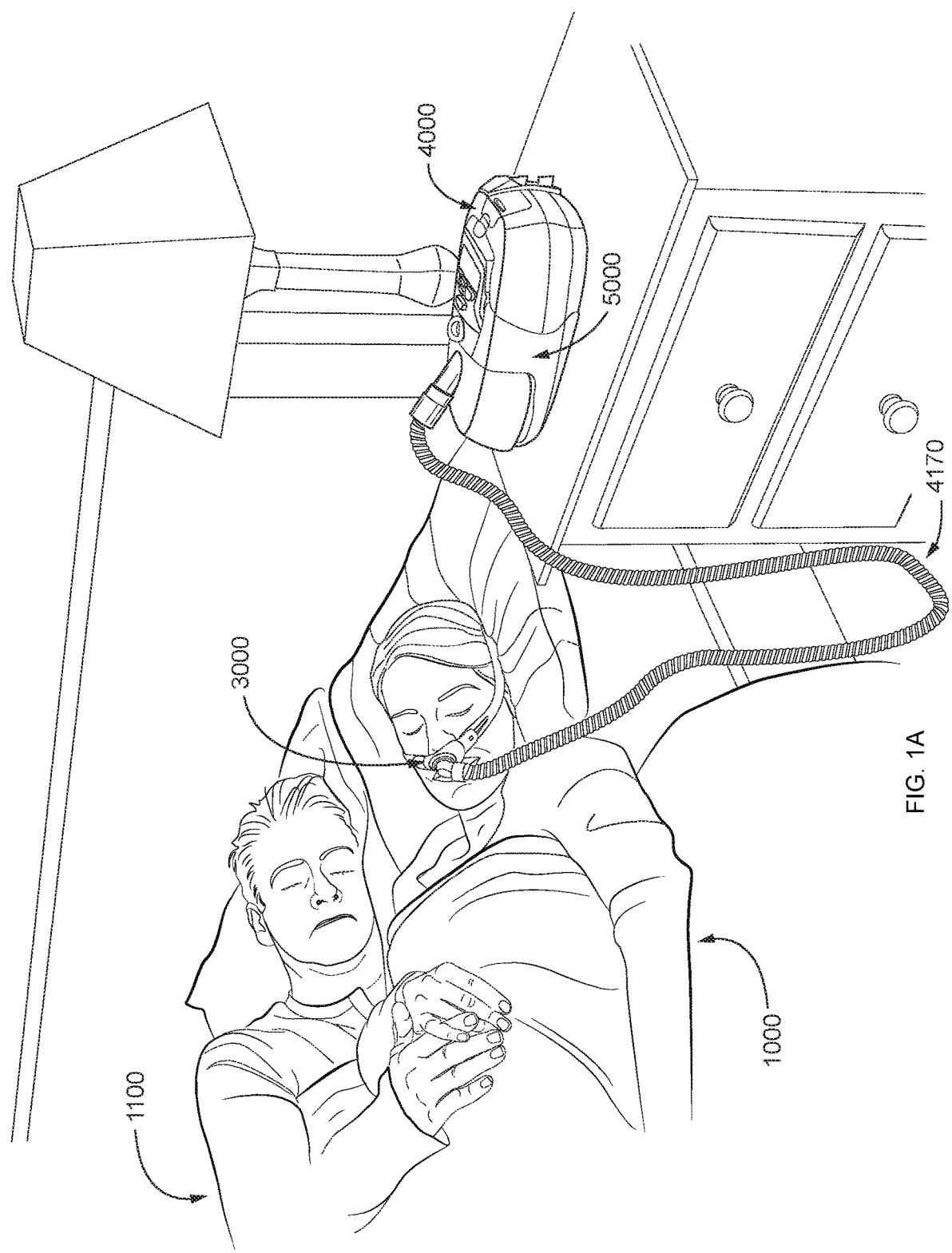
FIG. 1B shows a contactless sensor unit 7000 monitoring a sleeping patient 1000. The contactless sensor unit 7000 may be a Doppler radar movement sensor that provides a signal representing respiratory movement of the patient 1000, which signal may be used as a proxy for patient respiratory flow.
Figure 1B:
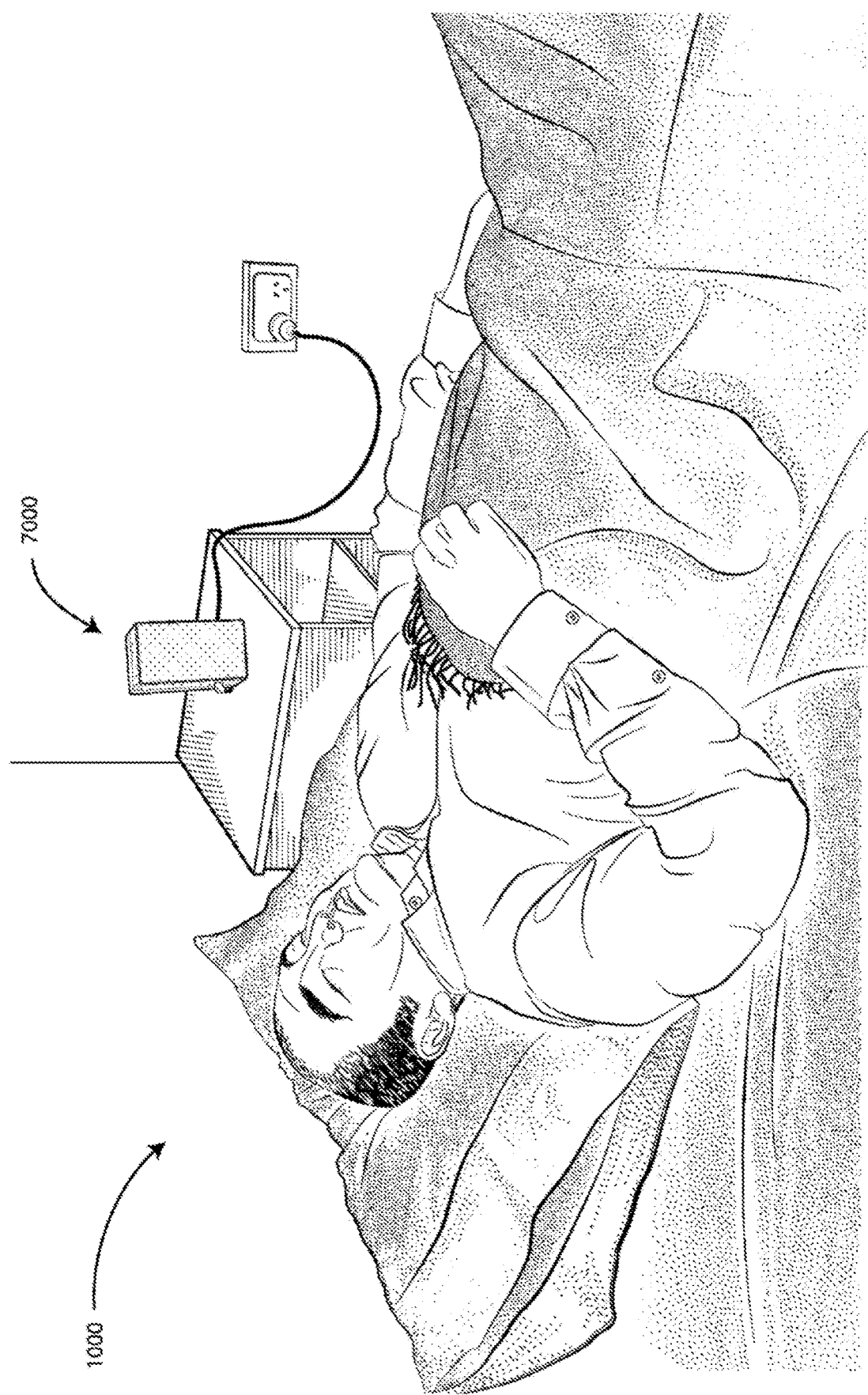
Figure 2A:
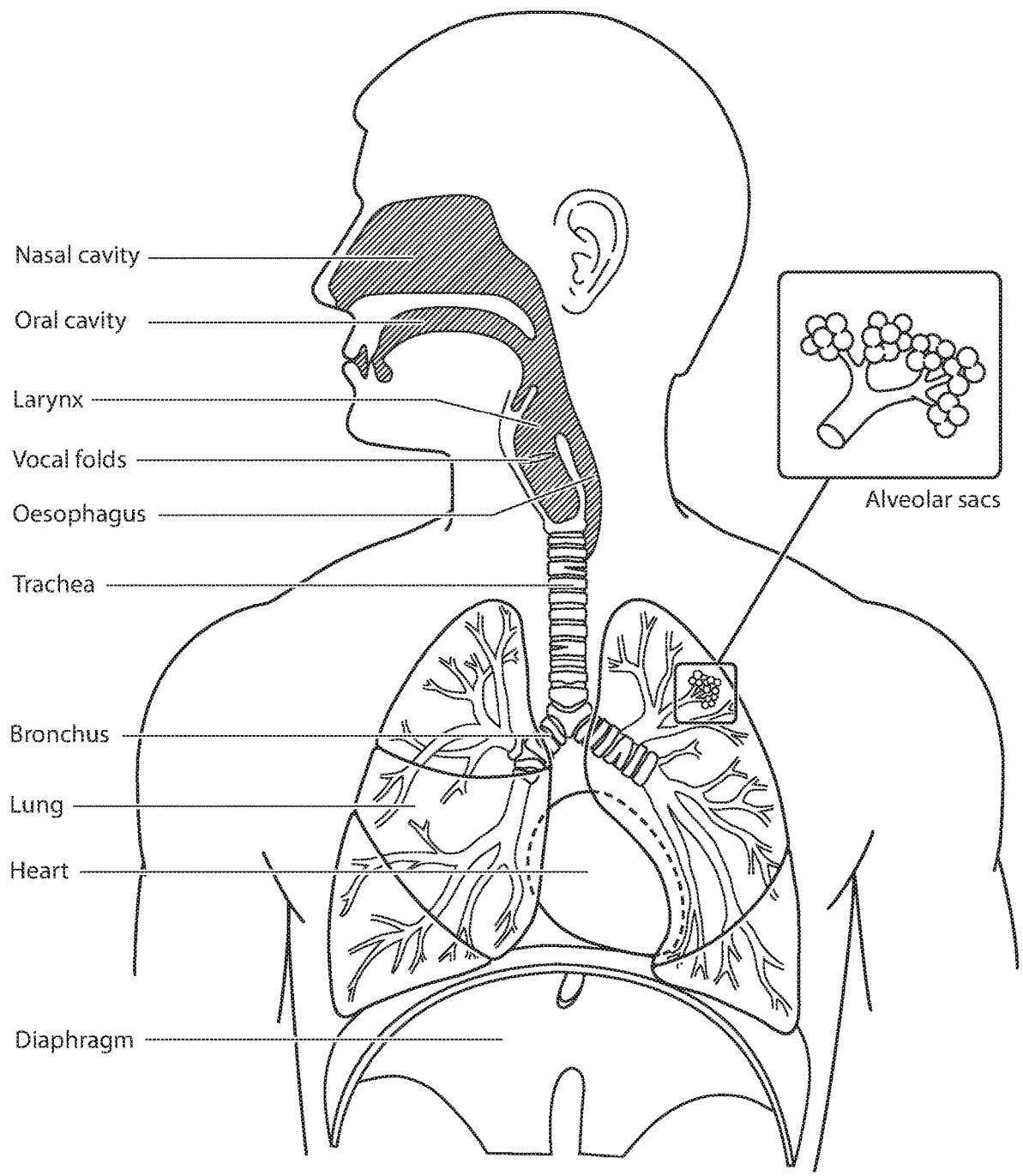
FIG. 2A shows an overview of a human respiratory system including the nasal and oral cavities, the larynx, vocal folds, oesophagus, trachea, bronchus, lung, alveolar sacs, heart and diaphragm.
Figure 2B:
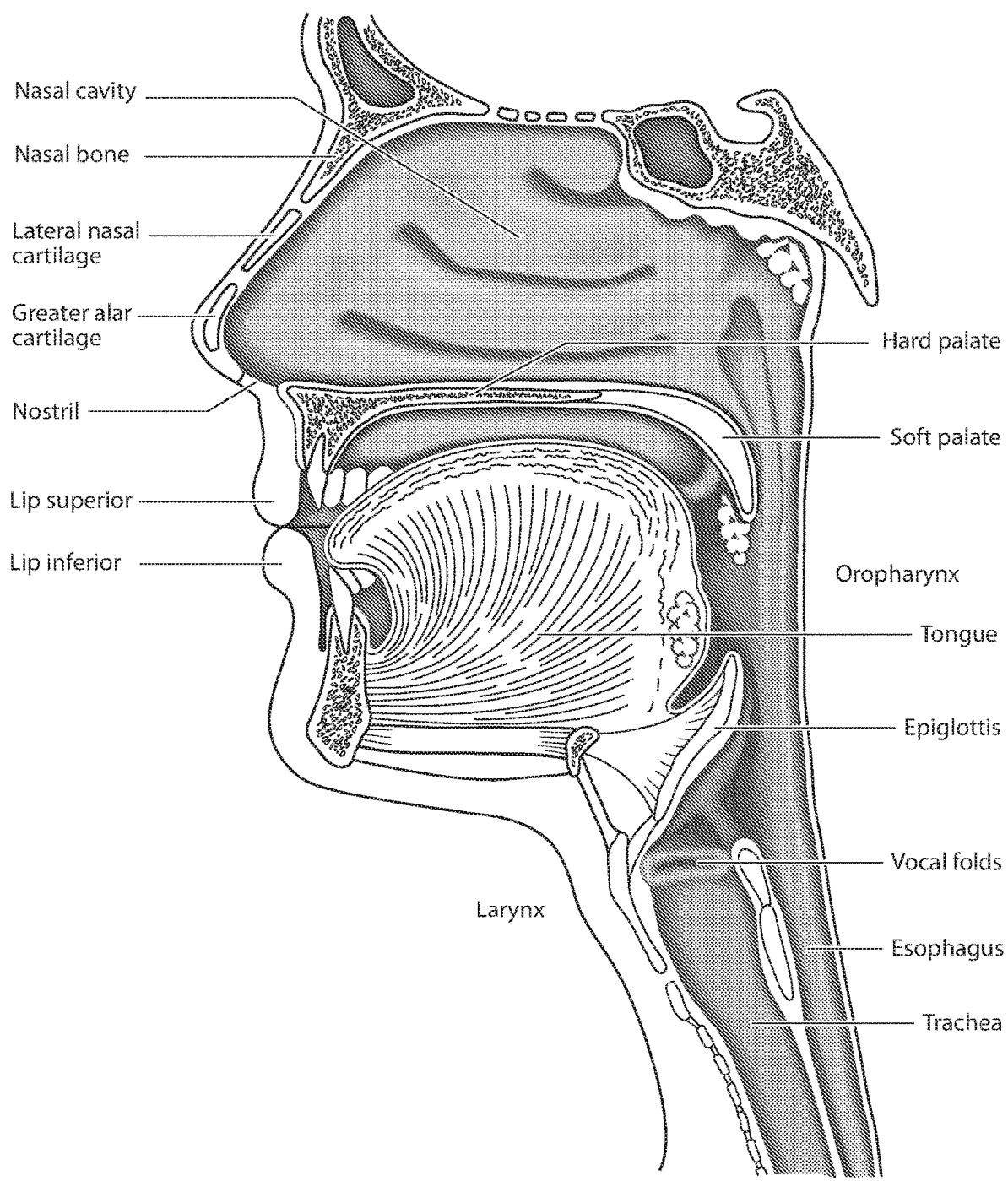
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 3:
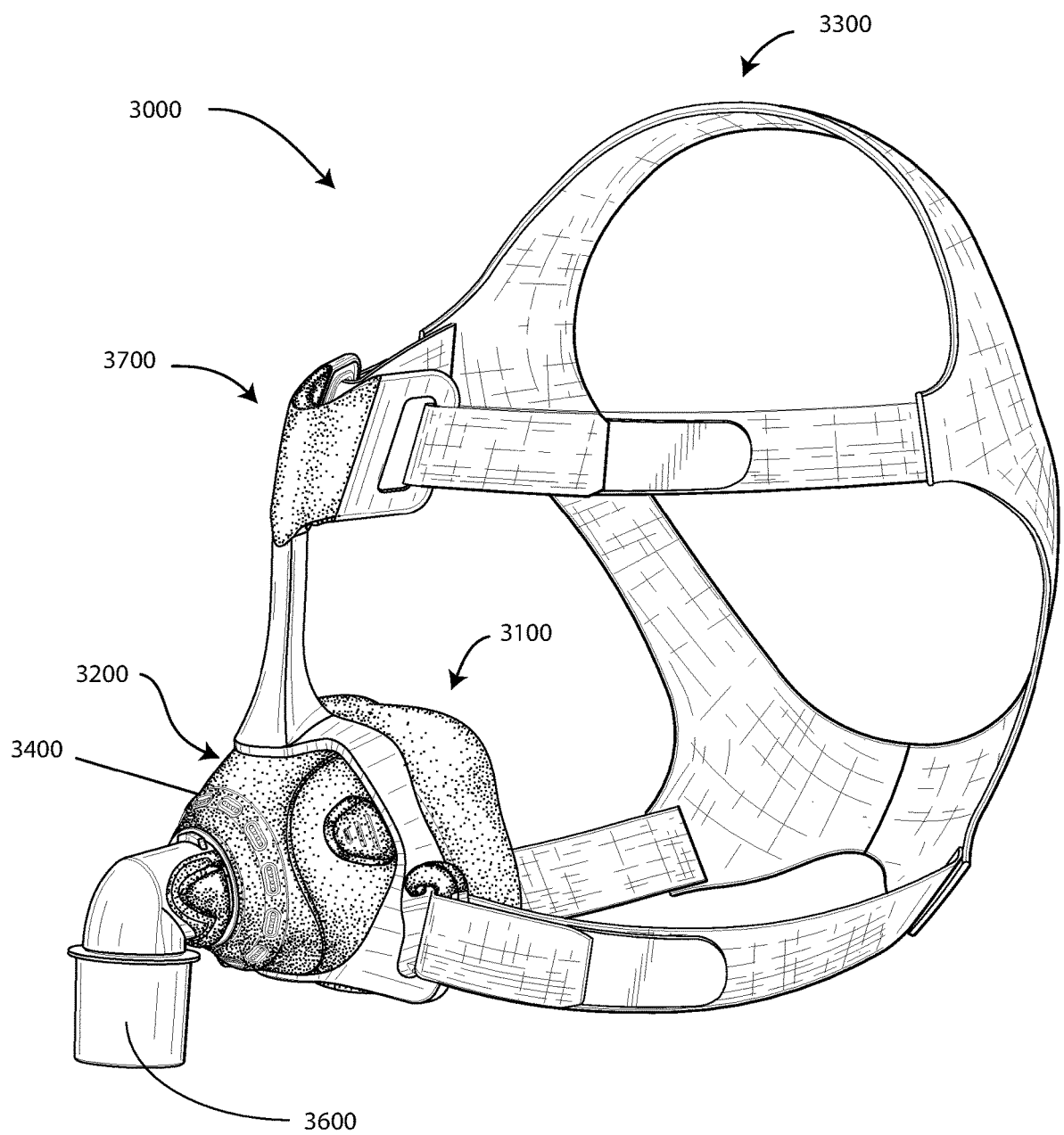
FIG. 3 shows a patient interface in accordance with one form of the present technology.
Figure 4A:
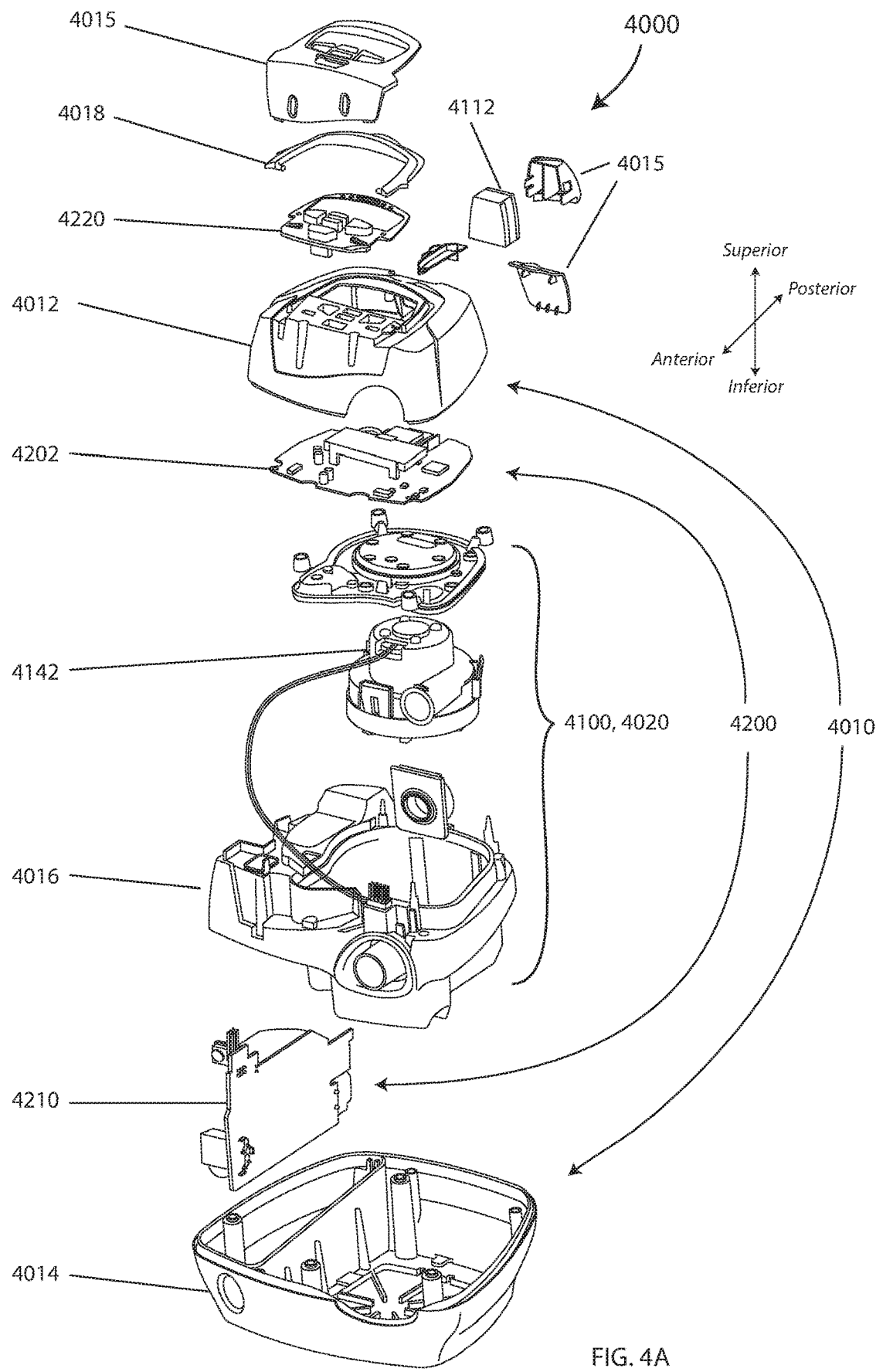
FIG. 4A shows a PAP device in accordance with one form of the present technology.
Figure 4B:
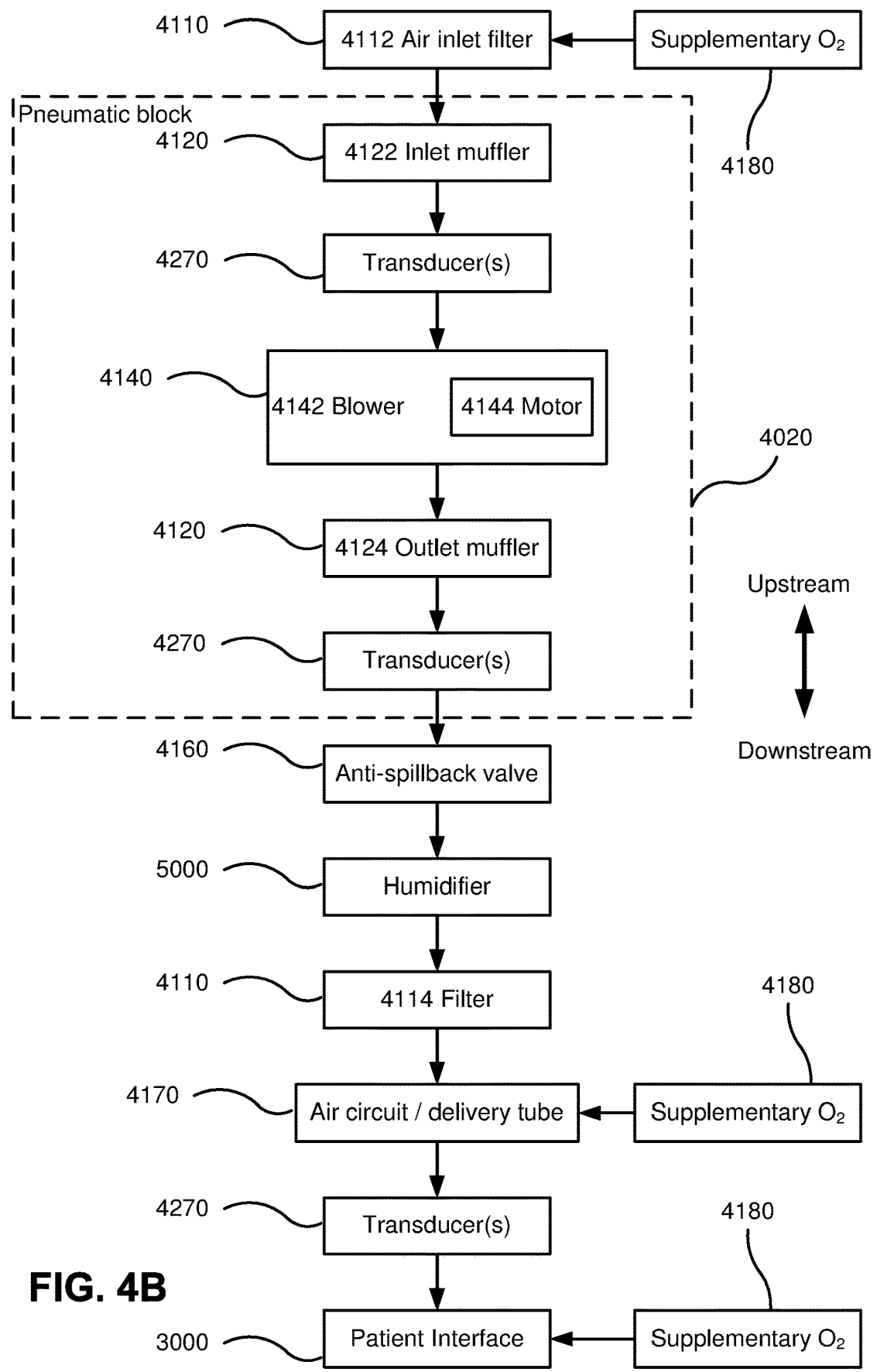
FIG. 4B shows a schematic diagram of the pneumatic circuit of a PAP device in accordance with one form of the present technology. The directions of upstream and downstream are indicated.
Figure 4C:
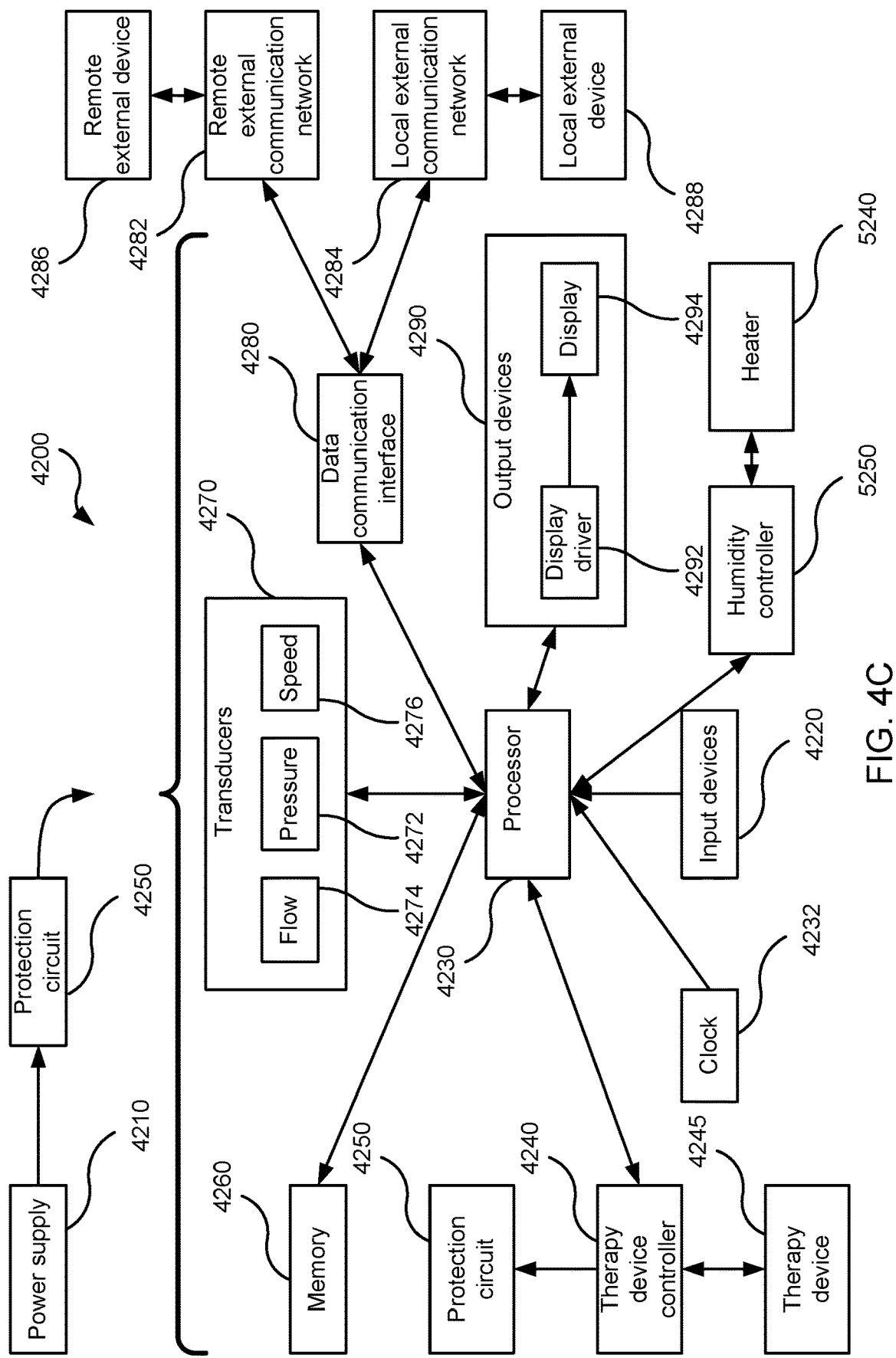
FIG. 4C shows a schematic diagram of the electrical components of a PAP device in accordance with one aspect of the present technology.
Figure 4D:
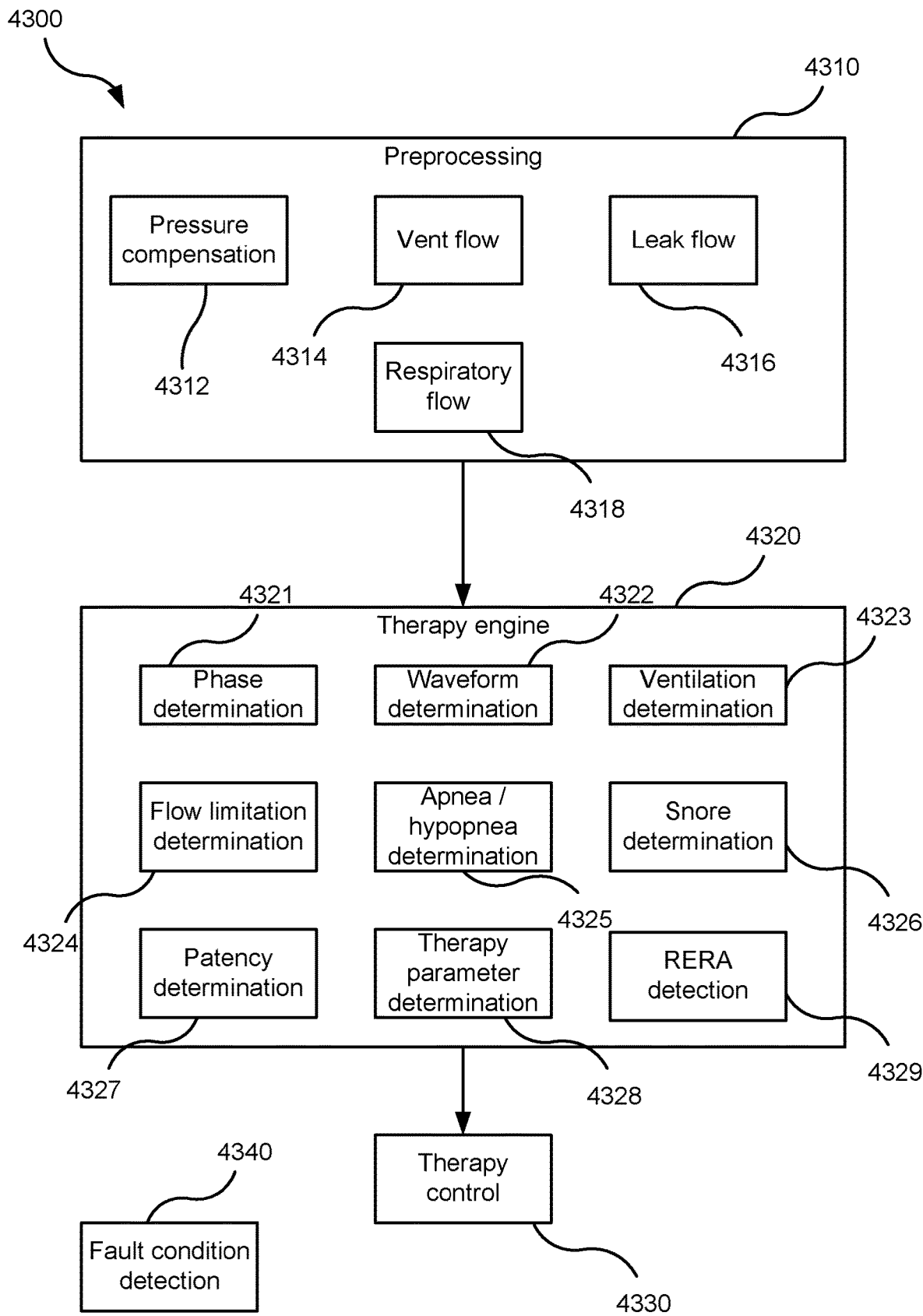
FIG. 4D shows a schematic diagram of the algorithms implemented in a PAP device in accordance with an aspect of the present technology. In this figure, arrows with solid lines indicate an actual flow of information, for example via an electronic signal.
Figure 4E:
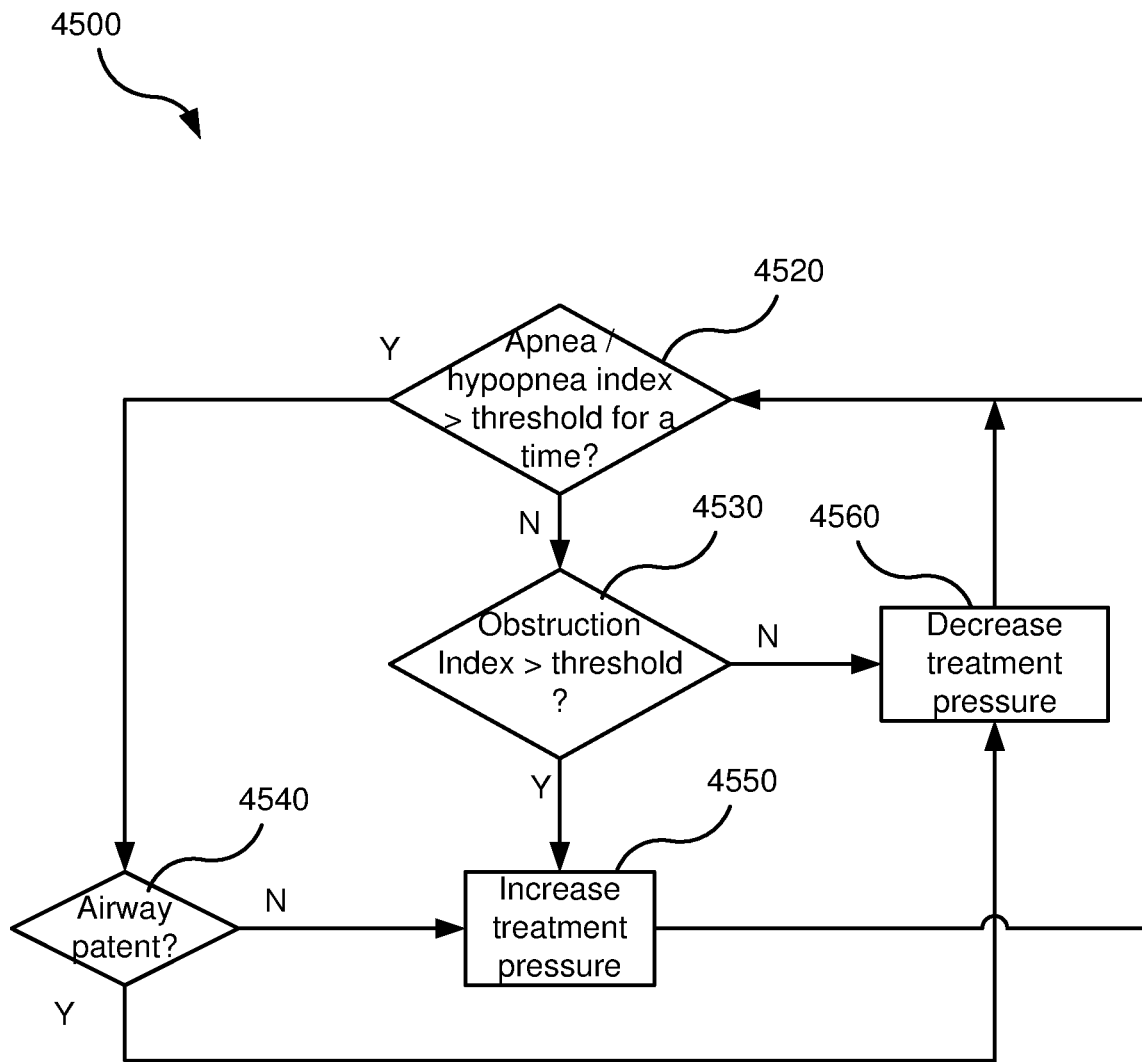
FIG. 4E is a flow chart illustrating a method carried out by the therapy engine of FIG. 4D in accordance with one aspect of the present technology.
Figure 4F:
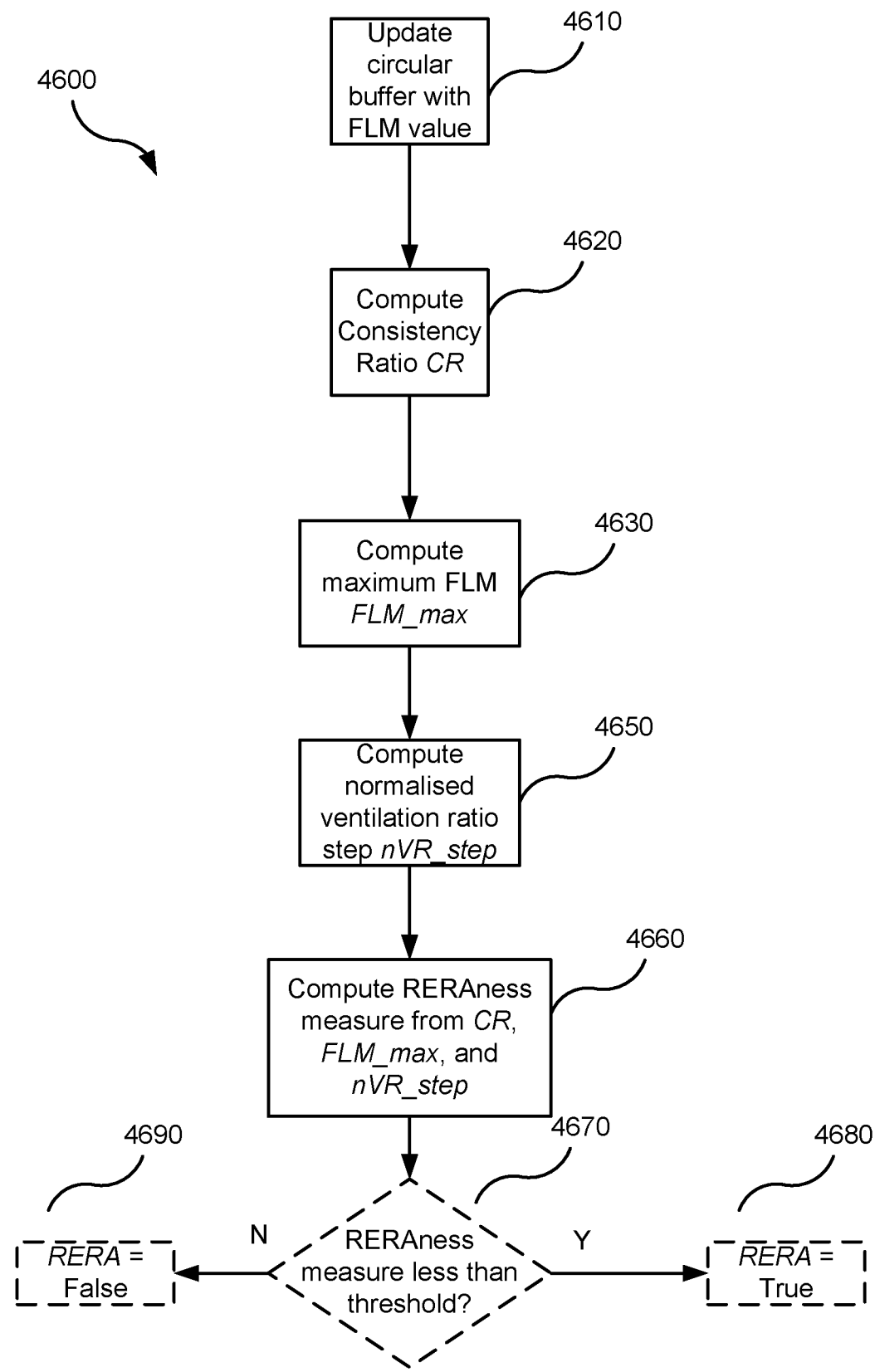
FIG. 4F is a flow chart illustrating a method that may be implemented for the RERA detection algorithm of FIG. 4D in one form of the present technology.
Figure 5:
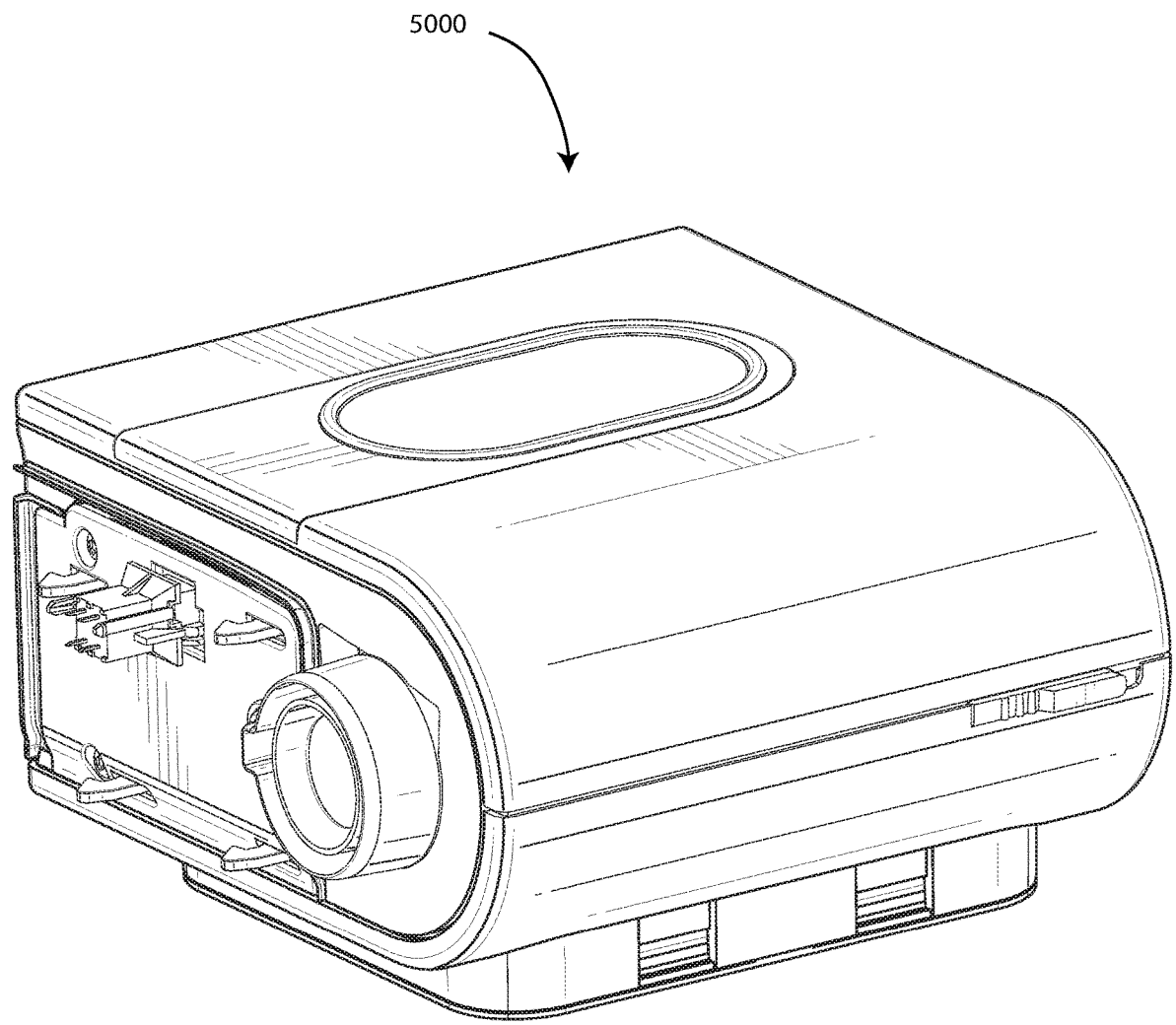
FIG. 5 shows a humidifier in accordance with one aspect of the present technology.
Figure 7:
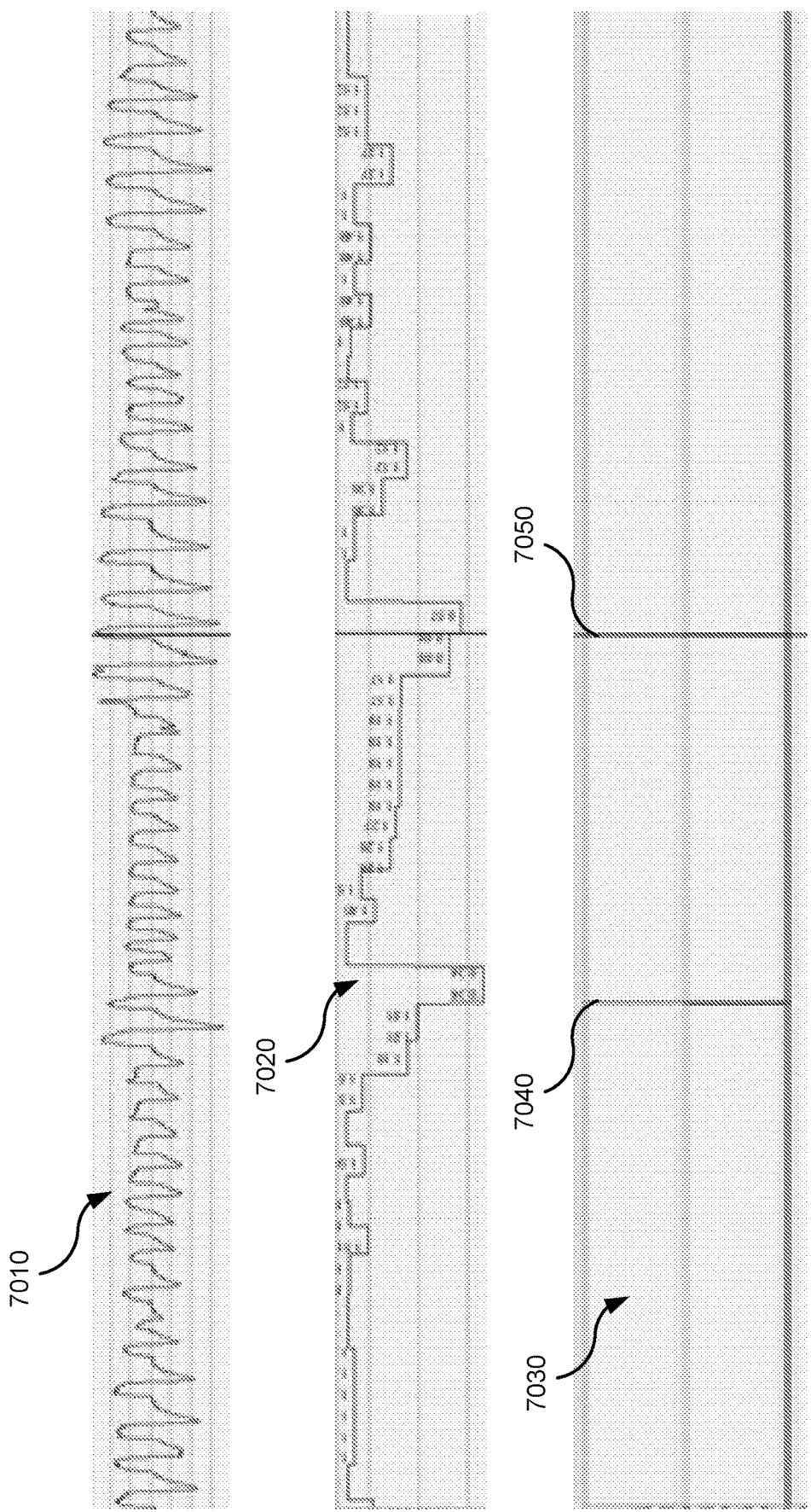

FIG. 7 contains three graphs illustrating the output of the RERA detection algorithm illustrated in FIG. 4F on an example flow signal.

Figure 8:
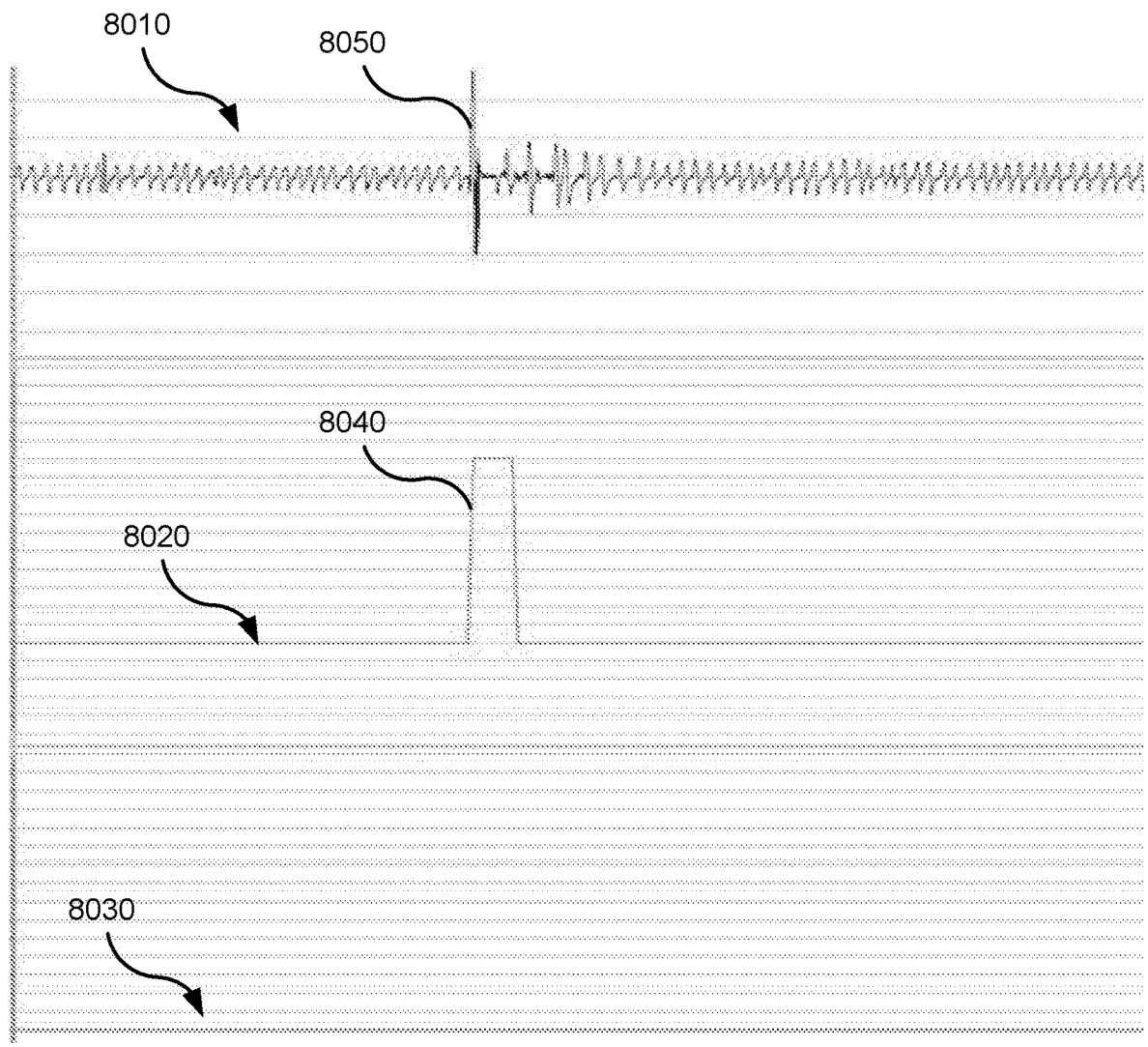

FIG. 8 contains three graphs illustrating the output of the RERA detection algorithm illustrated in FIG. 4F and a previous RERA detection algorithm on an example flow signal.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

8.1 Therapy

In one form, the present technology comprises a method for treating a respiratory disorder comprising the step of applying positive pressure to the entrance of the airways of a patient 1000.

In certain embodiments of the present technology, a supply of air at positive pressure is provided to the nasal passages of the patient via one or both nares.

8.2 Treatment Systems

In one form, the present technology comprises apparatus for treating a respiratory disorder. The apparatus may comprise a PAP device 4000 for supplying pressurised respiratory gas, such as air, to the patient 1000 via an air delivery tube leading to a patient interface 3000.

8.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, a connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

8.4 PAP Device

A PAP device 4000 in accordance with one aspect of the present technology comprises mechanical and pneumatic components 4100 and electrical components 4200 and is programmed to execute one or more algorithms 4300. The PAP device 4000 preferably has an external housing 4010, preferably formed in two parts, an upper portion 4012 of the external housing 4010, and a lower portion 4014 of the external housing 4010. In alternative forms, the external housing 4010 may include one or more panel(s) 4015. Preferably the PAP device 4000 comprises a chassis 4016 that supports one or more internal components of the PAP device 4000. In one form a pneumatic block 4020 is supported by, or formed as part of the chassis 4016. The PAP device 4000 may include a handle 4018.

The pneumatic path of the PAP device 4000 preferably comprises an inlet air filter 4112, an inlet muffler 4122, a controllable pressure device 4140 capable of supplying air at positive pressure (preferably a blower 4142), and an outlet muffler 4124. One or more sensors or transducers 4270 are included in the pneumatic path.

The preferred pneumatic block 4020 comprises a portion of the pneumatic path that is located within the external housing 4010.

The PAP device 4000 preferably has an electrical power supply 4210, one or more input devices 4220, a processor 4230, a therapy device controller 4240, a therapy device 4245, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the PAP device 4000 may include more than one PCBA 4202.

8.4.1 PAP Device Mechanical & Pneumatic Components 4100

8.4.1.1 Air Filter(s) 4110

A PAP device in accordance with one form of the present technology may include an air filter 4110, or a plurality of air filters 4110.

In one form, an inlet air filter 4112 is located at the beginning of the pneumatic path upstream of a pressure device 4140.

In one form, an outlet air filter 4114, for example an antibacterial filter, is located between an outlet of the pneumatic block 4020 and a patient interface 3000.

8.4.1.2 Muffler(s) 4120

In one form of the present technology, an inlet muffler 4122 is located in the pneumatic path upstream of a pressure device 4140.

In one form of the present technology, an outlet muffler 4124 is located in the pneumatic path between the pressure device 4140 and a patient interface 3000.

8.4.1.3 Pressure Device 4140

In a preferred form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 litres/minute, at a positive pressure in a range from about 4 cmH$_2$O to about 20 cmH$_2$O, or in other forms up to about 30 cmH$_2$O.

The pressure device 4140 is under the control of the therapy device controller 4240.

8.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

8.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit 4170

An air circuit 4170 in accordance with an aspect of the present technology is constructed and arranged to allow a flow of air or breathable gasses between the pneumatic block 4020 and the patient interface 3000.

8.4.1.7 Supplemental Oxygen 4180

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

8.4.2 PAP Device Electrical Components 4200

8.4.2.1 Power Supply 4210

In one form of the present technology power supply 4210 is internal of the external housing 4010 of the PAP device 4000. In another form of the present technology, power supply 4210 is external of the external housing 4010 of the PAP device 4000.

In one form of the present technology power supply 4210 provides electrical power to the PAP device 4000 only. In another form of the present technology, power supply 4210 provides electrical power to both PAP device 4000 and humidifier 5000.

8.4.2.2 Input Devices 4220

In one form of the present technology, a PAP device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the processor 4230.

In one form the input device 4220 may be constructed and arranged to allow a person to select a value and/or a menu option.

8.4.2.3 Processor 4230

In one form of the present technology, the processor 4230 is a processor suitable to control a PAP device 4000 such as an x86 INTEL processor.

A processor 4230 suitable to control a PAP device 4000 in accordance with another form of the present technology includes a processor based on ARM Cortex-M processor from ARM Holdings. For example, an STM32 series microcontroller from ST MICROELECTRONICS may be used.

Another processor 4230 suitable to control a PAP device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the processor 4230 for the PAP device 4000. For example a processor from the MSP430 family of microcontrollers, manufactured by TEXAS INSTRUMENTS, may be used.

The processor 4230 is configured to receive input signal(s) from one or more transducers 4270, and one or more input devices 4220.

The processor 4230 is configured to provide output signal(s) to one or more of an output device 4290, a therapy device controller 4240, a data communication interface 4280 and humidity controller 5250.

In some forms of the present technology, the processor 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a PAP device 4000. However, in some forms of the present technology the processor(s) may be implemented discretely from the flow generation components of the PAP device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein.

The processor 4230 of the PAP device 4000 is programmed to execute one or more algorithms 4300, preferably including a pre-processing module 4310, a therapy engine module 4320, a therapy control module 4330, and a fault condition module 4340.

8.4.2.4 Clock 4232

Preferably PAP device 4000 includes a clock 4232 that is connected to processor 4230.

8.4.2.5 Therapy Device Controller 4240

In one form of the present technology, therapy device controller 4240 is a therapy control module 4330 that forms part of the algorithms 4300 executed by the processor 4230.

In one form of the present technology, therapy device controller 4240 is a dedicated motor control integrated circuit. For example, in one form a MC33035 brushless DC motor controller, manufactured by ONSEMI is used.

8.4.2.6 Protection Circuits 4250

Preferably a PAP device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

8.4.2.7 Memory 4260

In accordance with one form of the present technology the PAP device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, PAP device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300. The processor 4230 is configured to execute such instructions stored on the non-transitory computer readable storage medium.

8.4.2.8 Transducers 4270

Transducers may be internal of the PAP device 4000, or external of the PAP device 4000. External transducers may be located for example on or form part of the air circuit 4170, e.g. at the patient interface 3000. External transducers may be in the form of non-contact sensors such as a Doppler radar movement sensor that transmit or transfer data to the PAP device 4000.

8.4.2.8.1 Flow Transducer 4274

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In one example, a signal representing total flow Qt from the flow transducer 4274 is received by the processor 4230.

8.4.2.8.2 Pressure Transducer 4272

A pressure transducer 4272 in accordance with the present technology is located in fluid communication with the pneumatic path. An example of a suitable pressure transducer 4272 is a sensor from the HONEYWELL ASDX series. An alternative suitable pressure transducer is a sensor from the NPA Series from GENERAL ELECTRIC.

In use, a signal from the pressure transducer 4272 is received by the processor 4230. In one form, the signal from the pressure transducer 4272 is filtered prior to being received by the processor 4230.

8.4.2.8.3 Motor Speed Signal 4276

In one form of the present technology a motor speed signal 4276 is generated. A motor speed signal 4276 is preferably provided by therapy device controller 4240. Motor speed may, for example, be generated by a speed sensor, such as a Hall effect sensor.

8.4.2.9 Data Communication Interface 4280

In one preferred form of the present technology, a data communication interface 4280 is provided, and is connected to processor 4230. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor 4230. In another form, data communication interface 4280 is an integrated circuit that is separate from processor 4230.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

8.4.2.10 Output Device 4290 Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

8.4.2.10.1 Display Driver 4292

A display driver 4292 receives as an input the characters, symbols, or images intended for display on the display 4294, and converts them to commands that cause the display 4294 to display those characters, symbols, or images.

8.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.4.3 PAP Device Algorithms 4300

8.4.3.1 Pre-Processing Module 4310

A pre-processing module 4310 in accordance with the present technology receives as an input, raw data from a transducer, for example a flow or pressure transducer, and preferably performs one or more process steps to calculate one or more output values that will be used as an input to another module, for example a therapy engine module 4320.

In one form of the present technology, the output values include the interface or mask pressure Pm, the respiratory flow Qr, and the leak flow Ql.

In various forms of the present technology, the pre-processing module 4310 comprises one or more of the following algorithms: pressure compensation 4312, vent flow 4314, leak flow 4316, and respiratory flow 4318.

8.4.3.1.1 Pressure Compensation 4312

In one form of the present technology, a pressure compensation algorithm 4312 receives as an input a signal indicative of the pressure in the pneumatic path proximal to an outlet of the pneumatic block 4020. The pressure compensation algorithm 4312 estimates the pressure drop in the air circuit 4170 and provides as an output an estimated pressure, Pm, in the patient interface 3000.

8.4.3.1.2 Vent Flow 4314

In one form of the present technology, a vent flow estimation algorithm 4314 receives as an input an estimated pressure, Pm, in the patient interface 3000 and estimates a vent flow of air, Qv, from a vent 3400 in a patient interface 3000.

8.4.3.1.3 Leak Flow 4316

In one form of the present technology, a leak flow algorithm 4316 receives as an input a total flow, Qt, and a vent flow Qv, and provides as an output a leak flow Ql by calculating an average of Qt–Qv over a period sufficiently long to include several breathing cycles, e.g. about 10 seconds.

In one form, the leak flow algorithm 4316 receives as an input a total flow, Qt, a vent flow Qv, and an estimated pressure, Pm, in the patient interface 3000, and provides as an output a leak flow Ql by calculating a leak conductance, and determining a leak flow Ql to be a function of leak conductance and pressure, Pm. Preferably leak conductance is calculated as the quotient of low pass filtered non-vent flow Qt–Qv, and low pass filtered square root of pressure Pm, where the low pass filter time constant has a value sufficiently long to include several breathing cycles, e.g. about 10 seconds.

8.4.3.1.4 Respiratory Flow 4318

In one form of the present technology, a respiratory flow algorithm 4318 receives as an input a total flow, Qt, a vent flow, Qv, and a leak flow, Ql, and estimates a respiratory flow of air, Qr, to the patient, by subtracting the vent flow Qv and the leak flow Ql from the total flow Qt.

8.4.3.2 Therapy Engine Module 4320

In one form of the present technology, a therapy engine module 4320 receives as inputs one or more of a pressure, Pm, in a patient interface 3000, and a respiratory flow of air to a patient, Qr, and provides as an output one or more therapy parameters.

8.4.3.2.1 Phase Determination 4321

In one form of the present technology, a phase determination algorithm 4321 receives as an input a signal indicative of respiratory flow, Qr, and provides as an output a phase of a breathing cycle of a patient 1000.

In one form, the phase output is a discrete variable with values of either inhalation or exhalation. The phase output is determined to have a discrete value of inhalation when a respiratory flow Qr has a positive value that exceeds a positive threshold. In one form, a phase is determined to have a discrete value of exhalation when a respiratory flow Qr has a negative value that is more negative than a negative threshold.

In one form, the phase output is a discrete variable with values of one of inhalation, mid-inspiratory pause, and exhalation.

In one form, the phase output is a continuous variable, for example varying from 0 to 1, or 0 to $2\pi$, or 0° to 360°.

8.4.3.2.2 Waveform Determination 4322

In one form of the present technology, a control module 4330 controls a therapy device 4245 to provide an approximately constant positive airway pressure throughout a respiratory cycle of a patient.

In another form of the present technology, a control module 4330 controls a therapy device 4245 to provide positive airway pressure according to a predetermined waveform of pressure vs phase. In one form, the waveform is maintained at an approximately constant level for all values of phase. In one form, the waveform is a square wave, having a higher value for some values of phase, and a lower level for other values of phase.

In one form of the present technology a waveform determination algorithm 4322 receives as an input a value indicative of current patient ventilation, Vent, and provides as an output a waveform of pressure vs. phase.

8.4.3.2.3 Ventilation Determination 4323

In one form of the present technology, a ventilation determination algorithm 4323 receives an input a respiratory flow Qr, and determines a measure indicative of current patient ventilation, Vent.

In one form, the ventilation determination algorithm 4323 determines the measure of current patient ventilation, Vent, as half the low-pass filtered absolute value of respiratory flow, Qr. In one implementation, the low-pass filter has a time constant of three minutes.

In one form, the ventilation determination algorithm 4323 also computes a ventilation ratio VR that is a measure of a "big breath". Values of VR greater than 1 may be taken as indicating breaths that are large compared to the medium term ventilation. In one implementation, the ventilation determination algorithm 4323 computes the ventilation ratio VR as the mean inspiratory flow rate divided by the current ventilation, Vent. The mean inspiratory flow rate may be computed as the mean tidal volume (the average of inspiratory and expiratory tidal volumes for the current breath) divided by the inspiratory time Ti.

8.4.3.2.4 Determination of Inspiratory Flow Limitation 4324

In one form of the present technology, a processor executes one or more algorithms 4324 for the determination of a measure of inspiratory flow limitation in the current breath. Examples of inspiratory flow limitation are illustrated in FIGS. 6B to 6G.

In one form, the inspiratory flow limitation determination algorithm 4324 receives as an input the respiratory flow signal Qr and provides as an output a measure of the extent to which the inspiratory portion of the current breath exhibits inspiratory flow limitation. This measure is referred to as the flow limitation measure (FLM).

In one implementation, the inspiratory portion of each breath is identified by a zero-crossing detector. A number of evenly spaced points (for example, sixty-five), representing points in time, are interpolated by an interpolator along the inspiratory flow-time curve for each breath. The curve described by the points is then scaled by a scaler to have unity length (duration/period) and unity area to remove the effects of changing respiratory rate and depth. The scaled breaths are then compared in a comparator with a pre-stored template representing a normal unobstructed breath, similar to the inspiratory portion of the breath shown in FIG. 6A. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by processor 4230 for the preceding several inspiratory events. This is repeated over the same inspiratory events for the second such point, and so on. Thus, for example, sixty-five scaled data points are generated by processor 4230, and represent a moving average of the preceding several inspiratory events, e.g. three events. The moving average of continuously updated values of the (e.g. sixty-five) points are hereinafter called the "scaled flow", designated as Qs(t). Alternatively, a single inspiratory event can be utilised rather than a moving average.

From the scaled flow Qs, two shape factors relating to the determination of partial obstruction are calculated.

Shape factor 1 is the ratio of the mean of the middle (e.g. thirty-two) scaled flow points to the mean overall (e.g. sixty-five) scaled flow points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical user.

Shape factor 2 is calculated as the RMS deviation from unit scaled flow, taken over the middle (e.g. thirty two) points. An RMS deviation of about 0.2 units is taken to be normal. An RMS deviation of zero is taken to be a totally flow-limited breath. The closer the RMS deviation is to zero, the more the breath will be taken to be flow limited.

The flow limitation measure FLM is a combination of shape factor 1 and shape factor 2, mapped to the range [0, 1], such that the closer the value of FLM is to 1, the more flow-limited is the inspiratory portion of the breath.

In variations of the above implementation, the number of sampled points, breaths and middle points may differ from those described above. Furthermore, the threshold values can other than those described above.

In another implementation, the inspiratory flow limitation determination algorithm 4324 receives as input the respiratory flow signal Qr, the ventilation Vent, and the ventilation ratio VR, and computes the flow limitation measure FLM. In one such implementation, the computation of the flow limitation measure FLM is carried out as described in PCT Patent Publication no. WO 2008/138040, assigned to ResMed Ltd., the disclosure of which is hereby incorporated herein by reference. This implementation produces a value of FLM in the range [0, 1], such that the closer the value of FLM is to 1, the more flow-limited is the inspiratory portion of the breath.

8.4.3.2.5 Determination of Apneas and Hypopneas 4325

In one form of the present technology, a processor 4230 executes one or more algorithms 4325 for the determination of the presence of apneas and/or hypopneas.

Preferably the one or more algorithms 4325 receive as an input a respiratory flow signal Qr and provide as an output a flag that indicates that an apnea or a hypopnea has been detected.

In one form, an apnea will be said to have been detected when a function of respiratory flow Qr falls below a flow threshold for a predetermined period of time. The function may determine a peak flow, a relatively short-term mean flow, or a flow intermediate of relatively short-term mean and peak flow, for example an RMS flow. The flow threshold may be a relatively long-term measure of flow.

In one form, a hypopnea will be said to have been detected when a function of respiratory flow Qr falls below a second flow threshold for a predetermined period of time. The function may determine a peak flow, a relatively short-term mean flow, or a flow intermediate of relatively short-term mean and peak flow, for example an RMS flow. The second flow threshold may be a relatively long-term measure of flow. The second flow threshold is greater than the flow threshold used to detect apneas.

8.4.3.2.6 Determination of Snore 4326

In one form of the present technology, a processor 4230 executes one or more snore algorithms 4326 for the detection of snore.

In one form the snore algorithm 4326 receives as an input a respiratory flow signal Qr and provides as an output a metric of the extent to which snoring is present.

Preferably the algorithm 4326 comprises the step of determining the intensity of the flow signal in the range of 30-300 Hz. Further preferably, algorithm 4326 comprises a step of filtering the respiratory flow signal Qr to reduce background noise, e.g. the sound of airflow in the system from the blower.

8.4.3.2.7 Determination of Airway Patency 4327

In one form of the present technology, a processor 4230 executes one or more algorithms 4327 for the determination of airway patency.

In one form, airway patency algorithm 4327 receives as an input a respiratory flow signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency algorithm 4327 receives as an input a respiratory flow signal Qr, and determines the presence or absence of a cardiogenic signal. The absence of a cardiogenic signal is taken to be an indication of a closed airway.

8.4.3.2.8 Determination of Therapy Parameters 4328

In one form of the present technology, processor 4230 executes one or more algorithms 4328 for the determination of therapy parameters.

In one form, the algorithm 4328 receives as an input one of more of the following:
  i. A measure of inspiratory flow limitation;
  ii. A measure of the presence of apnea and/or hypopnea;
  iii. A measure of the presence of snore; and
  iv. A measure of the patency of the airway;
      and generates a treatment pressure Pt as a function of the current time t.

FIG. 4E is a flow chart illustrating a method 4500 carried out by the processor 4230 as one implementation of the algorithm 4328. The method 4500 starts at step 4520, at which the processor 4230 compares the measure of the presence of apnea/hypopnea with a first threshold, and determines whether the measure of the presence of apnea/hypopnea has exceeded the first threshold for a predetermined period of time, indicating an apnea/hypopnea is occurring. If so, the method 4500 proceeds to step 4540; otherwise, the method 4500 proceeds to step 4530. At step 4540, the processor 4230 compares the measure of airway patency with a second threshold. If the measure of airway patency exceeds the second threshold, indicating the airway is patent, the detected apnea/hypopnea is deemed central, and the method 4500 proceeds to step 4560; otherwise, the apnea/hypopnea is deemed obstructive, and the method 4500 proceeds to step 4550.

At step 4530, the processor 4230 compares the measure of flow limitation with a third threshold. If the measure of flow limitation exceeds the third threshold, indicating inspiratory flow is limited, the method 4500 proceeds to step 4550; otherwise, the method 4500 proceeds to step 4560.

At step 4550, the processor 4230 increases the treatment pressure Pt by a predetermined pressure increment ΔP, provided the increased treatment pressure Pt would not exceed an upper limit Pmax. In one implementation, the predetermined pressure increment ΔP and upper limit Pmax are 1 $cmH_2O$ and 20 $cmH_2O$ respectively. The method 4500 then returns to step 4520.

At step 4560, the processor 4230 decreases the treatment pressure Pt by a decrement, provided the decreased treatment pressure Pt would not fall below a lower limit Pmin.

The method 4500 then returns to step 4520. In one implementation, the decrement is proportional to the value of Pt−Pmin, so that the decrease in Pt to the lower limit Pmin in the absence of any detected events is exponential. In one implementation, the constant of proportionality is set such that the time constant τ of the exponential decrease of Pt is between 10 and 20 minutes, and the lower limit Pmin is 4 $cmH_2O$. Alternatively, the decrement in Pt could be predetermined, so the decrease in Pt to the lower limit Pmin in the absence of any detected events is linear.

8.4.3.2.9 Detection of RERAs 4329

In one form of the present technology, one or more processors may implement one or more of the methodologies, or aspects thereof, described herein for detection of a RERA. For example, a processor 4230 executes one or more RERA detection algorithms 4329 for detection of respiratory effort related arousals (RERAs) implementing the methodologies described herein. The one or more processors may, for example, be implemented in a PAP device that can provide a respiratory treatment, in a computing device that analyses previously-recorded flow data input to the computer, or in a monitor/detection device having one or more sensor(s) to measure and analyse signals indicative of patient respiration, such as a non-contact sensor, and which may or may not provide a respiratory or other treatment.

In one form, the RERA detection algorithm 4329 receives as an input the current flow limitation measure FLM (from the flow limitation determination algorithm 4324) and the current ventilation ratio VR (from the ventilation determination algorithm 4323) and provides as an output an indication of the occurrence of a RERA. Thus, a RERA may be detected based on one or more measures derived from sensor signals, such as a flow sensor or respiration sensor. For example, the RERA indication may be determined based of a measure of sleep disordered breathing events and/or a measure of ventilation.

In one implementation, the RERA indication is a continuously-valued measure (referred to as a "RERAness" measure) indicating the degree of confidence of occurrence of a RERA. In another implementation, the RERAness measure is compared with a predetermined threshold to provide a Boolean-valued indication of occurrence of a RERA.

In one implementation, the RERA detection algorithm 4329 is based on the following methodology: if there has been flow limitation recently (e.g., the flow limitation measure FLM is greater than a threshold, (e.g., 0)) followed by a step change in ventilation (indicating a sudden "big breath"), then a RERA is indicated.

Known methods of detecting RERAs according to this methodology can result in false positives because the ventilation step change and flow limitation measure FLM are multiplied to provide the RERAness measure. In cases where the ventilation step change is large and the flow limitation measure FLM is inappropriately elevated (if only by a small amount), such methods would indicate a RERA when there actually was only a normal arousal rather than an arousal related to respiratory effort.

To reduce the number of false positives compared to known methods, a RERA detection algorithm 4329 according to one form of the present technology evaluates recent consistency of elevated flow limitation, as well as a step change in ventilation indicating a sudden big breath. This reduces the number of false positives significantly compared to previously known methods, as further described below with reference to FIG. 8.

FIG. 4F is a flow chart illustrating a method 4600 of detecting RERAs that may be implemented by the RERA detection algorithm 4329 according to one form of the present technology. The method 4600 starts at step 4610, which updates a data structure or buffer, such as a circular buffer, with the current value FLM of the flow limitation measure. The data structure contains a small number of the most recent values of the flow limitation measure FLM, which may be on a per breath basis. In one implementation, the data structure contains the three most recent values of the flow limitation measure FLM, such as from the three most recent breaths. In the circular buffer case, step 4610 overwrites the oldest flow limitation measure FLM in the circular buffer with the current flow limitation measure FLM.

Step 4620 follows, which computes a measure of consistency of inspiratory flow limitation over recent breaths (e.g., the recent flow limitation measures represented in the circular buffer). In one implementation, the measure of consistency is the Consistency Ratio CR, computed as the fraction of flow limitation measures in the circular buffer that exceed a predetermined threshold. In one implementation, the threshold is 0.1. In step 4630 the maximum flow limitation measure in the circular buffer, FLM_max is determined.

Next, in step 4650, a measure of a step change in ventilation indicating a sudden "big breath" is computed. In one implementation, the measure is the normalised ventilation ratio step nVR_step, computed as the difference VR_step between the current value VR of the ventilation ratio and the previous value of the ventilation ratio, mapped to the range [0, 1]. In one implementation, this mapping is carried out according to the following function:

$$nVR\_step = \begin{cases} 0, & VR\_step < 0.1 \\ \dfrac{\sqrt{VR\_step}}{\sqrt{2}}, & 0.1 \leq VR\_step \leq 2 \\ 1, & VR\_step > 2 \end{cases}$$

In step 4660, the RERAness measure is computed by calculating a distance between the three-dimensional point (CR, FLM_max, nVR_step) and the corner point of a three-dimensional cube. In one implementation, the corner point is the three-dimensional point (1, 1, 1). In one implementation, the distance is a Euclidean distance. A smaller value of the RERAness measure indicates a greater degree of confidence of occurrence of a RERA.

In an optional step 4670, the RERAness measure is compared with a predetermined threshold to provide a variable (e.g, a Boolean-valued variable (RERA)) indicating an occurrence of a RERA. In one implementation, this threshold has the value 0.75. If the RERAness measure is less than the predetermined threshold ("Y" at step 4670), step 4680 sets RERA to True. Otherwise ("N" at step 4670), step 4690 sets RERA to False.

FIG. 7 contains three graphs illustrating the output of the RERA detection algorithm 4329 on an example flow signal. The top graph 7010 shows an example respiratory flow signal Qr with a duration of approximately three minutes. The middle graph 7020 shows a continuously-valued RERAness measure obtained from the respiratory flow signal Qr in the top graph 7010 using the above-described RERA detection algorithm 4329. The bottom graph 7030 contains the Boolean-valued indication RERA (represented as a binary variable) obtained by comparing the continuously-valued RERAness measure in the middle graph 7020 with a threshold of 0.75. The value of RERA is generally False (0) but rises to True (1) at two points 7040, 7050 when the continuously-valued RERAness measure in the middle graph 7020 falls below 0.75.

In one form of the present technology, the number of positive detections (e.g., with Boolean indications RERA) provided by the RERA detection algorithm 4329 during an interval, together with the number of apneas and/or number of hypopneas detected by the apnea/hypopnea determination algorithm 4325 during the interval may be applied to calculate an RDI (Respiratory Disturbance Index) as a function of an interval measure such as interval duration (e.g., divided by interval duration). In one form the RDI is computed by the following equation:

RDI=(#_of_RERAs+#_of_Apneas+#_of_Hypopneas)/interval_duration

Where:
 #_of_RERA is a count of RERAs, such as with the RERA variable in a time interval;
 #_of_Apneas is a count of apneas detected in the time interval;
 #_of_Hypopneas is a count of hypopneas detected in the time interval; and
 interval_duration is the length of the time interval (e.g., in hours).

Alternatively, the RERA indication could be reported by a PAP device 4000 as an indication of the effectiveness of the therapy. Such reporting may be made to external devices through the data communication interface 4280, or to a user via the output devices 4290.

In yet another form, the RERAness measure computed by the RERA detection algorithm 4329 could be implemented as input into the therapy parameter determination algorithm 4328. For example, the RERAness measure may be averaged over a certain time frame, such as per hour, and the result may be applied in an "outer loop controller" to set a threshold (or gain) for the flow limitation measure to affect the target treatment pressure. An example of an outer loop controller is described in PCT Publication no. WO 2005/051470 (PCT/AU2004/001652) assigned to ResMed Ltd., the disclosure of which is hereby incorporated herein by reference. For example, a patient who arouses from sleep as determined by the RERAness measure may be treated more aggressively (e.g., a higher pressure change) in response to subsequently detected sleep disordered breathing events when compared to the response (e.g. a lower pressure change) to detected sleep disordered breathing events that coincide with an absence of arousal indicated by the RERAness measure.

As mentioned above, the RERA detection algorithm 4329 according to one form of the present technology evaluates recent consistency of elevated flow limitation, as well as a step change in ventilation indicating a sudden big breath. This may reduce the number of false positives significantly compared to previously known methods. FIG. 8 contains three graphs illustrating the output of the RERA detection algorithm 4329 and a previous RERA detection algorithm on an example flow signal. The top graph 8010 shows an example respiratory flow signal Qr with a duration of approximately nine minutes and no RERAs. The middle graph 8020 shows a Boolean-valued indication of RERAs obtained from the respiratory flow signal Qr in the top graph 8010 using a previous RERA detection algorithm. The bottom graph 8030 shows a Boolean-valued indication of RERAs obtained from the respiratory flow signal Qr in the top graph 8010 using the RERA detection algorithm 4329. The middle graph 8020 shows one indication of a RERA at the point 8040. This is caused by the large breath 8050 which provides a one-off elevation in the flow limitation measure. However, the bottom graph 8030 does not show any indication of a RERA at the same point 8040, because there is no consistency of elevated flow limitation at that point.

8.4.3.3 Control Module 4330

A control module 4330 receives the one or more therapy parameters computed by the therapy parameter determination module 4328, and controls a therapy device 4245 in accordance with the one or more therapy parameters.

In one form of the present technology, the control module 4330 receives as an input a treatment pressure Pt, and controls a therapy device 4245 to deliver that pressure.

In one form of the present technology, the control module 4330 receives as an input an EPAP pressure and an IPAP pressure, and controls a therapy device 4245 to deliver those respective pressures.

8.4.3.4 Detection of Fault Conditions 4340

In one form of the present technology, a processor executes one or more methods for the detection of fault conditions. Preferably the fault conditions detected by the one or more methods includes at least one of the following:
Power failure (no power, or insufficient power)
Transducer fault detection
Failure to detect the presence of a component
Operating parameters outside recommended ranges (e.g. pressure, flow, temperature, $PaO_2$)
Failure of a test alarm to generate a detectable alarm signal.

Upon detection of the fault condition, the corresponding algorithm signals the presence of the fault by one or more of the following:
Initiation of an audible, visual &/or kinetic (e.g. vibrating) alarm
Sending a message to an external device
Logging of the incident

8.4.3.5 Therapy Device 4245

In a preferred form of the present technology, the therapy device 4245 is under the control of the control module 4330 to deliver therapy to a patient 1000.

Preferably the therapy device 4245 is a pressure device 4140.

8.5 Glossary

For the purposes of the present technology disclosure, in certain forms of the present technology, one or more of the following definitions may apply. In other forms of the present technology, alternative definitions may apply.

8.5.1 General

Air: In certain forms of the present technology, air supplied to a patient may be atmospheric air, and in other forms of the present technology atmospheric air may be supplemented with oxygen.

Continuous Positive Airway Pressure (CPAP): CPAP treatment will be taken to mean the application of a supply of air or breathable gas to the entrance to the airways at a pressure that is continuously positive with respect to atmosphere, and approximately constant through a respiratory cycle of a patient. In some forms, the pressure at the entrance to the airways will vary by a few centimetres of water within a single respiratory cycle, for example being higher during inhalation and lower during exhalation. In some forms, the pressure at the entrance to the airways will be slightly higher during exhalation, and slightly lower during inhalation.

Automatic Positive Airway Pressure (APAP): CPAP treatment using a pressure that is continually adjustable between minimum and maximum limits, depending on the presence or absence of indications of SDB events.

Positive Airway Pressure (PAP) device: A device for providing a supply of air at positive pressure to the airways.

8.5.2 Aspects of PAP Devices

Air circuit: A conduit or tube constructed and arranged in use to deliver a supply of air or breathable gas between a PAP device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

Blower or flow generator: A device that delivers a flow of air at a pressure above ambient pressure.

Controller: A device or portion of a device that adjusts an output based on an input. For example one form of controller has a variable that is under control—the control variable—that constitutes the input to the device. The output of the device is a function of the current value of the control variable, and a set point for the variable.

Transducers: A device for converting one form of energy or signal into another. A transducer may be a sensor or detector for converting mechanical energy (such as movement) into an electrical signal. Examples of transducers include pressure sensors, flow sensors, carbon dioxide ($CO_2$) sensors, oxygen ($O_2$) sensors, effort sensors, movement sensors, noise sensors, a plethysmograph, and cameras.

8.5.3 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Breathing rate: The rate of spontaneous respiration of a patient, usually measured in breaths per minute.

Duty cycle: The ratio of inhalation time, Ti, to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation (or partial obstruction) will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of inspiratory flow limited waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

Positive End-Expiratory Pressure (PEEP): The pressure above atmosphere in the lungs that exists at the end of expiration.

Peak flow (Qpeak): The maximum value of flow during the inspiratory portion of the respiratory flow waveform.

Respiratory (air)flow, (air)flow, patient (air)flow (Qr): These synonymous terms may be understood to refer to an estimate of the "true respiratory (air)flow", which is the instantaneous respiratory flow being experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the amount (e.g., total) of gas being exchanged by the patient's respiratory system, including inspiratory and/or expiratory flow, per unit time. When expressed as a volume per minute, this quantity is often referred to as "minute ventilation". Minute ventilation is sometimes given simply as a volume, understood to be the volume per minute.

8.5.4 PAP Device Parameters

Flow rate: The instantaneous volume (or mass) of air delivered per unit time. While flow rate and ventilation have the same dimensions of volume or mass per unit time, flow rate is measured over a much shorter period of time. Flow may be nominally positive for the inspiratory portion of a breathing cycle of a patient, and hence negative for the expiratory portion of the breathing cycle of a patient. In some cases, a reference to flow rate will be a reference to a scalar quantity, namely a quantity having magnitude only. In other cases, a reference to flow rate will be a reference to a vector quantity, namely a quantity having both magnitude and direction. Flow will be given the symbol Q. Total flow, Qt, is the flow of air leaving the PAP device. Vent flow, Qv, is the flow of air leaving a vent to allow washout of exhaled gases. Leak flow, Ql, is the flow rate of unintentional leak from a patient interface system. Respiratory flow, Qr, is the flow of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face.

Pressure: Force per unit area. Pressure may be measured in a range of units, including $cmH_2O$, $g$-$f/cm^2$, hectopascal. $1 cmH_2O$ is equal to 1 $g$-$f/cm^2$ and is approximately 0.98 hectopascal. In this specification, unless otherwise stated, pressure is given in units of $cmH_2O$. The pressure in the patient interface, or mask pressure, is given the symbol Pm. A target value for the mask pressure, referred to as the treatment pressure, is given the symbol Pt.

8.6 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

| 8.7 REFERECE SIGNS LIST | |
|---|---|
| patient | 1000 |
| patient interface | 3000 |
| structure | 3100 |
| plenum chamber | 3200 |
| structure | 3300 |
| vent | 3400 |
| connection port | 3600 |
| forehead support | 3700 |
| PAP device | 4000 |
| external housing | 4010 |
| upper portion | 4012 |
| portion | 4014 |
| panel | 4015 |
| chassis | 4016 |
| handle | 4018 |
| pneumatic block | 4020 |
| pneumatic component | 4100 |
| air filter | 4110 |

-continued

| 8.7 REFERECE SIGNS LIST | |
|---|---|
| inlet air filter | 4112 |
| outlet air filter | 4114 |
| muffler | 4120 |
| inlet muffler | 4122 |
| outlet muffler | 4124 |
| pressure device | 4140 |
| blower | 4142 |
| motor | 4144 |
| back valve | 4160 |
| air circuit | 4170 |
| supplemental oxygen | 4180 |
| PAP device electrical components | 4200 |
| PCBA | 4202 |
| electrical power supply | 4210 |
| input device | 4220 |
| processor | 4230 |
| clock | 4232 |
| therapy device controller | 4240 |
| therapy device | 4245 |
| protection circuit | 4250 |
| memory | 4260 |
| transducer | 4270 |
| pressure transducer | 4272 |
| flow transducer | 4274 |
| motor speed signal | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithms | 4300 |
| pre-processing module | 4310 |
| pressure compensation algorithm | 4312 |
| vent flow determination algorithm | 4314 |
| leak flow algorithm | 4316 |
| respiratory flow determination algorithm | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| patency determination algorithm | 4327 |
| therapy parameter determination algorithm | 4328 |
| RERA detection algorithm | 4329 |
| therapy control module | 4330 |
| fault condition detection module | 4340 |
| method | 4500 |
| step | 4520 |
| step | 4530 |
| step | 4540 |
| step | 4550 |
| step | 4560 |
| method | 4600 |
| step | 4610 |
| step | 4620 |
| step | 4630 |
| step | 4650 |
| step | 4660 |
| optional step | 4670 |
| step | 4680 |
| step | 4690 |
| humidifier | 5000 |
| humidity controller | 5250 |
| contactless sensor unit | 7000 |
| top graph | 7010 |
| middle graph | 7020 |
| bottom graph | 7030 |
| point | 7040 |
| point | 7050 |
| top graph | 8010 |
| middle graph | 8020 |

-continued

| 8.7 REFERECE SIGNS LIST | |
|---|---|
| bottom graph | 8030 |
| RERA indication | 8040 |
| large breath | 8050 |

The invention claimed is:

1. A method in a processor for detecting a respiratory effort-related arousal in a respiratory airflow signal of a patient, the method comprising:

receiving or calculating in a processor a measure of consistency of inspiratory flow limitation over a plurality of recent breaths from the respiratory airflow signal;

receiving or calculating in the processor a measure of step change in ventilation of the patient indicating a sudden big breath;

. . . and generating in the processor a maximum measure of inspiratory flow limitation over said plurality of recent breaths,

. . .

controlling, in a controller of a flow generator, adjustment of the respiratory therapy using the parameter, the respiratory therapy produced by the flow generator.

2. The method according to claim 1, wherein the processor calculates the measure of consistency of inspiratory flow limitation over a plurality of recent breaths from the signal.

3. A method according to claim 2, wherein calculating the measure of consistency of inspiratory flow limitation comprises calculating a fraction of recent flow limitation measures that exceed a predetermined threshold.

4. The method according to claim 1 wherein the processor calculates the measure of step change in ventilation indicating a sudden big breath.

5. A method according to claim 4, wherein calculating the measure of step change in ventilation comprises calculating a difference between a current value of a ventilation ratio and a previous value of the ventilation ratio, wherein the ventilation ratio is computed as a mean inspiratory flow rate divided by a measure of current ventilation.

6. A method according to claim 5, wherein the measure of step change in ventilation is the difference mapped to a range [0, 1].

7. A method according to claim 5, . . . wherein the mean inspiratory flow rate is computed as an average of inspiratory and expiratory tidal volumes divided by an inspiratory time for a current breath.

8. A method according to claim 1, further comprising comparing the degree of confidence of occurrence of a respiratory effort-related arousal with a predetermined threshold to provide an indication of whether the patient is currently experiencing a respiratory effort-related arousal.

9. A method according to claim 8, further comprising calculating a respiratory disturbance index from a number of indications of respiratory effort-related arousals in a predetermined interval.

10. A non-transitory computer-readable memory storage medium having program instructions encoded thereon configured to cause a processor to perform a method of detecting a respiratory effort-related arousal in a respiratory airflow signal of a patient, the method program instructions comprising:

program instructions to generate a measure of consistency of inspiratory flow limitation over a plurality of recent breaths from the respiratory airflow signal;

program instructions to generate a measure of step change in ventilation of the patient indicating a sudden big breath; and

. . .

program instructions to generate a maximum measure of inspiratory flow limitation over said plurality of recent breaths, . . . control adjustment of the respiratory therapy using the parameter, the respiratory therapy produced by the flow generator.

11. A device for detecting a respiratory effort-related arousal in a respiratory airflow signal of a patient, the device comprising a sensor configured to provide a signal representative of patient respiratory airflow, a processor configured to generate an output indication of a detection of a respiratory effort- related arousal, wherein the processor is configured to:

generate a measure of consistency of inspiratory flow limitation over a plurality of recent breaths from the signal representative of patient respiratory airflow;

generate a measure of step change in ventilation of the patient indicating a sudden big breath;

. . . and generate a maximum measure of inspiratory flow limitation over said plurality of recent breaths, . . . controlling adjustment of the respiratory therapy using the parameter, the respiratory therapy produced by the flow generator.

* * * * *